United States Patent [19]

Tobitsuka et al.

[11] Patent Number: 5,306,712
[45] Date of Patent: Apr. 26, 1994

[54] FUNGICIDAL SILICON-CONTAINING COMPOUNDS AND THEIR AGROCHEMICAL AND MEDICINAL USES

[75] Inventors: Junzo Tobitsuka; Hideo Takeshiba; Yasuhiko Kondo; Hiroshi Ohta; Shigehiro Kato, all of Shiga, Japan

[73] Assignee: Sanyo Company, Limited, Tokyo, Japan

[21] Appl. No.: 957,269

[22] Filed: Oct. 6, 1992

[30] Foreign Application Priority Data

Oct. 9, 1991 [JP] Japan ................................. 3-262089

[51] Int. Cl.$^5$ .................. A01N 55/00; A61K 31/695; C07D 7/08
[52] U.S. Cl. ......................................... 514/63; 548/110
[58] Field of Search ............................ 548/110; 514/63

[56] References Cited

U.S. PATENT DOCUMENTS 5,134,152 7/1992 Takeshiba et al. .................. 514/383

FOREIGN PATENT DOCUMENTS 207590 1/1987 European Pat. Off. .
0435794 7/1991 European Pat. Off. .
2224278A 5/1990 United Kingdom .

OTHER PUBLICATIONS

Chemical Abstracts, vol. 116, 1992, Columbus, Ohio, US; Abstract No. 59045k, Konosu et al.
Hudrlik et al, Tetrahedron Letters, "Rearrangements of $\beta,\gamma$-Epoxysilanes to $\beta$-Silyl Aldehydes and Ketones", No. 1, 1976, pp. 29-32, Pergamon Press.

Primary Examiner—Patricia L. Morris
Attorney, Agent, or Firm—Frishauf, Holtz, Goodman & Woodward

[57] ABSTRACT

Compounds of formula (I):

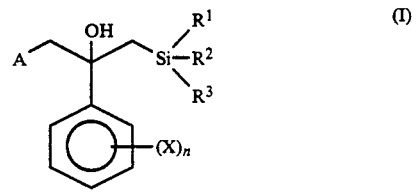

wherein: A is 1,2,4-triazol-1-yl or imidazol-1-yl; n is 0, 1, 2 or 3; X is halogen, phenyl, alkyl, haloalkyl, alkoxy, or haloalkoxy, or $(X)_n$ is alkylenedioxy; $R^1$ is alkyl or phenyl; and $R^2$ and $R^3$ are each alkyl; and salts thereof have valuable anti-fungal activity. Certain intermediates in the preparation of these compounds are also disclosed.

24 Claims, No Drawings

FUNGICIDAL SILICON-CONTAINING COMPOUNDS AND THEIR AGROCHEMICAL AND MEDICINAL USES

BACKGROUND TO THE INVENTION

The present invention relates to a series of new silicon-containing compounds which may be considered as 3-(1,2,4-triazol-1-yl or imidazol-1-yl)-2-hydroxy-2-(optionally substituted phenyl)-1-(tri-substituted silyl)propane derivatives, and which have valuable anti-fungal activities, which may be applied in the agricultural, horticultural and medical fields. The invention also provides methods and compositions using these compounds as well as processes for their preparation.

A number of tri-substituted silyl derivatives in which a triazolyl group is separated from a silicon atom by a carbon chain is known and some are known to have fungicidal properties. For example GB Patent Specification No. 2 175 301 describes a number of compounds which are said to be primarily plant growth regulators, but which are also said to have fungicidal properties. These compounds include, among many others, some trialkylsilyl derivatives, of which the only specific example is given in Example 11 and is 3-t-butyl-3-hydroxy-4-(1,2,4-triazol-1-yl) 1-trimethyl-silyl 1-pentyne, which differs from the compounds of the present invention in that it possesses a t-butyl group in place of the optionally substituted phenyl group of the compounds of the present invention, in that it is an alkyne, rather than alkane, derivative and in that it has a longer aliphatic chain than do the compounds of the present invention.

GB Patent Specification No. 2 224 278 also describes a number of compounds which are said to be plant growth regulators or fungicides, and which include, among many others, some trialkylsilyl derivatives. The only compound of this type specifically disclosed appears in Example 4 of that GB Specification and is 3 (2,4. dichlorophenyl)-3-hydroxy-4-(1,2,4-triazol-1-yl) 1-tri-methylsilyl-1-butene, which differs from the compounds of the present invention in that its aliphatic chain, and generally the aliphatic chains of the compounds in the GB Specification, is a butene, rather than propane, chain, that is, it is longer and it is unsaturated.

The closest prior art, however, is thought to be that described by J-F. Chollet et al. [Pestic. Sci., 29, 427–435 (1990)], where the compound identified as XX (Table 1, page 431), which may be called 4-(4-chlorophenyl)-4-hydroxy-5-(1,2,4-triazol-1-yl)-3-trimethylsilyl-1-pentene, differs from certain of the compounds of the present invention only in the presence of a vinyl substituent on the propane chain.

However, the prior art compounds, including those specifically described above, do not, in general, have sufficient activity. Moreover, one important property of compounds intended for use as agrochemical or pharmaceutical fungicides is that they should exhibit their activity at low dosages and should not induce any adverse side-effects. In addition, in the case of an agrochemical fungicide, it is a well recognized desideratum that the fungicide should have a systemic action, so that it may, for example, be applied as a coating to seeds or may be applied directly to crops or may be applied indirectly to submerged crops, such as to rice crops, and will be translocated throughout the plant.

Although each of the prior art compounds referred to above meets some of these requirements, none meets them all to a sufficient extent, and, in particular, most fail to exhibit any systemic activity at all, and, even in the one isomer of a prior art compound where some systemic activity is exhibited, this is lower than that of similar compounds of the present invention. As will be shown hereafter, the only compound included within the prior art to demonstrate any systemic activity is one isomer of 4-(4-chlorophenyl)-4-hydroxy-5-(1,2,4-triazol-1-yl)-3-trimethylsilyl-1-pentene, which isomer was not, in fact, separated from another, and systemically inactive, isomer by the prior art.

We have now surprisingly discovered a series of 3-(1,2,4-triazol-1-yl or imidazol-1-yl)-2-hydroxy-2-(optionally substituted phenyl)-1-(tri-substituted silyl)propane derivatives which are believed to have these desirable properties. This is the more surprising in that Chollet et al. suggest that unsaturated compounds, especially allylic compounds, are the most active, whereas the compounds of the present invention do not contain an unsaturated aliphatic group.

BRIEF SUMMARY OF INVENTION

It is, therefore, an object of the present invention to provide a series of novel silicon-containing triazolyl or imidazolyl derivatives of the type referred to.

It is a more specific object of the present invention to provide such derivatives, at least some of which have valuable fungicidal properties.

Other objects and advantages of the present invention will become apparent as the description proceeds.

The compounds of the present invention are those compounds of formula (I):

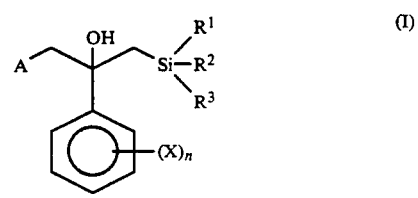

wherein:

A represents a 1,2,4-triazol-1-yl group or an imidazol-1-yl group;

n represents 0, 1, 2 or 3, and, when n represents 2 or 3, the groups represented by X may be the same or different;

X represents a halogen atom, a phenyl group, an alkyl group having from 1 to 6 carbon atoms, a haloalkyl group having from 1 to 6 carbon atoms and having at least one halogen atom, an alkoxy group having from 1 to 6 carbon atoms, or a haloalkoxy group having from 1 to 6 carbon atoms and having at least one halogen atom, or $(X)_n$ represents an alkylenedioxy group having 1 or 2 carbon atoms:

$R^1$ represents an alkyl group having from 1 to 4 carbon atoms or a phenyl group which is unsubstituted or is substituted by at least one halogen atom; and $R^2$ and $R^3$ are independently selected from the group consisting of alkyl groups having from 1 to 4 carbon atoms;

and salts thereof.

In addition, the invention also provides the following compounds which are valuable intermediates in the preparation of the compounds of formula (I). These intermediates are compounds of formula (I-2):

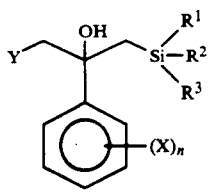

(I-2)

wherein: X, n, R$^1$, R$^2$ and R$^3$ are as defined above; and Y represents a chlorine, bromine or iodine atom, and compounds of formula (I-3):

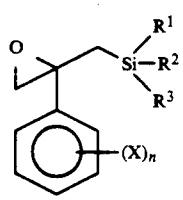

(I-3)

wherein: X, n, R$^1$, R$^2$ and R$^3$ are as defined above.

The invention also provides a pharmaceutical composition for the prevention or treatment of fungal infections, which comprises a fungicidally or fungistatically effective amount of an anti-fungal agent, wherein the anti-fungal agent is selected from the group consisting of compounds of formula (I) and pharmaceutically acceptable salts thereof, as defined above.

The invention still further provides a method for the prevention or treatment of fungal infections, which comprises applying or administering a fungicidally or fungistatically effective amount of an anti-fungal agent to an animal, e.g. a mammal, which may be human, wherein the anti-fungal agent is selected from the group consisting of compounds of formula (I) and pharmaceutically acceptable salts thereof, as defined above.

The invention also provides an agricultural composition for the protection of plants and plant reproductive matter from fungal attack, which composition comprises a fungicidally or fungistatically effective amount of a compound of formula (I) or a salt thereof, as defined above, in admixture with an agricultural carrier or diluent.

The invention still further provides a method of protecting plants and plant reproductive matter from fungal attack, which method comprises applying to said plants or plant reproductive matter or to a locus including the same a fungicidally or fungistatically effective amount of a compound of formula (I) or a salt thereof, as defined above.

The invention also provides several novel methods of preparing the compounds of the present invention, which are described in more detail hereafter.

DETAILED DESCRIPTION OF INVENTION

In the compounds of the present invention of formulae (I), (I-2) and (I-3), where X represents a halogen atom, this may be a fluorine, chlorine, bromine or iodine atom, and is more preferably a fluorine or chlorine atom, and most preferably a fluorine atom.

Where X represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl and hexyl groups. Of these, we prefer those alkyl groups having from 1 to 4 carbon atoms, preferably the methyl, ethyl, propyl, isopropyl, butyl and isobutyl groups, and most preferably the methyl and ethyl groups.

Where X represents a haloalkyl group, this has from 1 to 6 carbon atoms and may be a straight or branched chain alkyl group having one or more, preferably from 1 to 5 (or less if there are fewer substitutable positions), more preferably from 1 to 3, halogen substituents Examples include any of the alkyl groups exemplified above, but more preferably those having from 1 to 4 and most preferably 1 or 2 carbon atoms, in which one or more hydrogen atoms is replaced by a halogen atom (e.g. a fluorine, chlorine, bromine or iodine atom). Specific examples include the trifluoromethyl, trichloromethyl, difluoromethyl, dichloromethyl, dibromomethyl, fluoromethyl, chloromethyl, bromomethyl, iodomethyl, 2,2,2-trichloroethyl, 2,2,2-trifluoroethyl, 2-bromoethyl, 2-chloroethyl, 2-fluoroethyl, 2,2-dibromoethyl, 3-chloropropyl, 3,3,3-trifluoropropyl, 4-fluorobutyl, 5,5,5-trichloropentyl and 6,6,6-trifluorohexyl, groups, of which we prefer alkyl groups having from 1 to 3 carbon atoms which are substituted by from 1 to 3 halogen atoms (and, where there are 2 or 3 halogen atoms, these are the same), more preferably the methyl or ethyl groups which are substituted by from 1 to 3 fluorine or chlorine atoms. More preferred specific groups are the trifluoromethyl, trichloromethyl, difluoromethyl, 2-bromoethyl, 2-chloroethyl and 2-fluoroethyl groups, especially the trifluoromethyl group.

Where X represents an alkoxy group, this may be a straight or branched chain alkoxy group having from 1 to 6 carbon atoms. Examples of such groups include the methoxy, ethoxy, propoxy, isopropoxy, butoxy, isobutoxy, sec-butoxy, t-butoxy, pentyloxy, isopentyloxy, t-pentyloxy, neopentyloxy, hexyloxy, 2-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups. Of these, we prefer those alkoxy groups containing from 1 to 4 carbon atoms, especially the methoxy and ethoxy groups.

Where X represents a halogenated alkoxy group, this has from 1 to 6 carbon atoms and may be a straight or branched chain alkoxy group having one or more, preferably from 1 to 5 (or less if there are fewer substitutable positions), more preferably from 1 to 3, halogen substituents. Examples include any of the alkoxy groups exemplified above in which one or more hydrogen atoms is replaced by a halogen atom (e.g. a fluorine, chlorine, bromine or iodine atom). Specific examples include the trifluoromethoxy, trichloromethoxy, difluoromethoxy, dichloromethoxy, dibromomethoxy, fluoromethoxy, chloromethoxy, bromomethoxy, iodomethoxy, bromodifluoromethoxy, chlorodifluoromethoxy, 2,2,2-trichloroethoxy, 2,2,2-trifluoroethoxy, 2-bromoethoxy, 2-chloroethoxy, 2-fluoroethoxy, 2,2-dibromoethoxy, 3-chloropropoxy, 3,3,3-trifluoropropoxy, 4-fluorobutoxy, 5,5,5-trichloropentyloxy and 6,6,6-trifluorohexyloxy groups, of which we prefer the trifluoromethoxy group.

Alternatively, $(X)_n$ may represent an alkylenedioxy group having 1 or 2 carbon atoms, that is a methylenedioxy, ethylenedioxy or ethylidenedioxy group, to form with the two, preferably contiguous, carbon atoms of the benzene ring to which they are attached a 5- or 6-membered heterocyclic ring, i.e. a dioxolane or dioxane ring fused to the benzene ring, of which the 5-membered ring, that is the dioxolane ring, is preferred.

In the compounds of formula (I), A may represent a 1,2,4-triazol-1-yl group or an imidazol-1-yl group, preferably a 1,2,4-triazol-1-yl group.

In the compounds of formulae (I), (I-2) and (I-3), n may be 0, 1, 2 or 3, but is preferably 0, 1 or 2, more preferably 1 or 2, and most preferably 1.

In these compounds, where n is 0, the benzene ring is unsubstituted. Alternatively, where n is 1, 2 or 3, X preferably represents a fluorine atom, a chlorine atom, a bromine atom, an unsubstituted alkyl group having from 1 to 4 carbon atoms, a substituted alkyl group having from 1 to 4 carbon atoms and having from 1 to 3 halogen substituents, an unsubstituted alkoxy group having from 1 to 4 carbon atoms, or a substituted alkoxy group having from 1 to 4 carbon atoms and having from 1 to 3 halogen substituents. More preferably, where n is 1, 2 or 3, X represents a fluorine atom, a chlorine atom, a trifluoromethyl group or a methoxy group, or n may be 0. Still more preferably, n is 1 or 2 and X represents a fluorine atom or a chlorine atom, or n is 0. Most preferably, n is 1 or 2 and X represents a fluorine atom or a chlorine atom, especially a fluorine atom.

In the compounds of formulae (I), (I-2) and (I-3): where n is 3, X is preferably at the 2, 4 and 6 positions on the benzene ring; where n is 2, X is preferably at the 2 and 4 positions on the benzene ring; and where n is 1, X is preferably at the 2 or the 4 position on the benzene ring, more preferably the 4 position.

In the compounds of the present invention of formulae (I), (I-2) and (I-3) where $R^1$, $R^2$ or $R^3$ represents an alkyl group having from 1 to 4 carbon atoms, this may be a straight or branched chain group having from 1 to 4 carbon atoms, and examples include the methyl, ethyl, propyl, isopropyl, butyl, isobutyl, sec-butyl and t-butyl groups, more preferably the methyl and ethyl groups, and most preferably the methyl group.

Alternatively, $R^1$ may represent a phenyl group which may be unsubstituted or may be substituted by at least one halogen atom. There is no limit to the number of halogen substituents, except that imposed by the number of substitutable positions, that is 5. However, in general, we prefer from 1 to 3 substituents, more preferably 1 or 2, and most preferably 1. Nonetheless, we most prefer the unsubstituted phenyl group. Examples of such groups include the phenyl, 2-chlorophenyl, 3-chlorophenyl, 4-chlorophenyl, 2-fluorophenyl, 3-fluorophenyl, 4-fluorophenyl, 4-bromophenyl, 2,4-difluorophenyl, 2,6-difluorophenyl, 2,4-dichlorophenyl, 2,6-dichlorophenyl, 2-chloro-4-fluorophenyl, 4-chloro-2-fluorophenyl, 6-chloro-2-fluorophenyl, 2,4,6-trifluorophenyl and 2,4,6-trichlorophenyl groups, of which the 4-chlorophenyl, 4-fluorophenyl, 2,4-difluorophenyl, 2,4-dichlorophenyl, 2-chloro-4-fluorophenyl, 4-chloro-2-fluorophenyl and phenyl groups are preferred and the phenyl group itself is most preferred.

In the compound of formula (I-2), Y preferably represents a chlorine or bromine atom, more preferably a chlorine atom.

The following classes of compounds of formulae (I), (I-2) and (I-3) and salts thereof are preferred and are listed in increasing order of preference [in the compounds of formulae (I-2) and (I-3), the reference to the group represented by A should be ignored]:

(1) Those compounds in which:

A represents a 1,2,4-triazol-1-yl group;

n is 1 or 2, and X represents a fluorine atom, a chlorine atom, a bromine atom, an unsubstituted alkyl group having from 1 to 4 carbon atoms, a substituted alkyl group which has from 1 to 4 carbon atoms and which is substituted by from 1 to 3 halogen atoms, an unsubstituted alkoxy group having from 1 to 4 carbon atoms, or a substituted alkoxy group which has from 1 to 4 carbon atoms and which is substituted by from 1 to 3 halogen atoms; or n is 0; and $R^1$, $R^2$ and $R^3$ are independently selected from the group consisting of alkyl groups having 1 to 4 carbon atoms.

(2) Those compounds in which:

A represents a 1,2,4-triazol-1-yl group;

n is 1 or 2, and X represents a fluorine atom, a chlorine atom, a bromine atom, a trifluoromethyl group or a methoxy group, and the substituent represented by X is at the 2 position and/or the 4-position of the benzene ring; or n is 0; and $R^1$, $R^2$ and $R^3$ are independently selected from the group consisting of methyl groups and ethyl groups.

(3) Those compounds in which:

A represents a 1,2,4-triazol-1-yl group;

n is 1 or 2, and X represents a fluorine atom, a chlorine atom or a bromine atom, and the substituent represented by X is at the 2-position and/or the 4- position of the benzene ring; or n is 0; and $R^1$, $R^2$ and $R^3$ are independently selected from the group consisting of methyl groups and ethyl groups.

(4) Those compounds in which:

A represents a 1,2,4-triazol-1-yl group;

n is 1 or 2, and X represents a fluorine atom, or a chlorine atom, and the substituent represented by X is at the 2-position and/or the 4-position of the benzene ring; or n is 0; and $R^1$, $R^2$ and $R^3$ are all methyl groups.

The compounds of formula (I) of the present invention contain basic nitrogen atoms, and can thus form salts. Examples of such salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid. The compounds can also form adducts with organic acid amides, such as saccharin.

Specific examples of compounds of the present invention are shown in the following formulae (I-1) to (I-3), in which the various substituent groups are as defined in the corresponding one of Tables 1 to 3, i.e Table 1 relates to formula (I-1), Table 2 relates to formula (I-2) and Table 3 relates to formula (I-3). In the Tables, the following abbreviations are used:

| | |
|---|---|
| Bu | butyl |
| Et | ethyl |
| Imid | imidazol-1-yl |
| Me | methyl |
| Ph | phenyl |
| Pr | propyl |
| iPr | isopropyl |
| Triz | 1,2,4-triazol-1-yl |

$$\text{(I-1)}$$

$$\text{(I-2)}$$

$$\text{(I-3)}$$

TABLE 1

| Cpd. No. | A | (X)$_n$ | R$^1$ | R$^2$ | R$^3$ | W |
|---|---|---|---|---|---|---|
| 1-1 | Triz | H | Me | Me | Me | — |
| 1-2 | Triz | 4-Cl | Me | Me | Me | — |
| 1-3 | Triz | 4-F | Me | Me | Me | — |
| 1-4 | Triz | 4-Br | Me | Me | Me | — |
| 1-5 | Triz | 4-Me | Me | Me | Me | — |
| 1-6 | Triz | 4-CF$_3$ | Me | Me | Me | — |
| 1-7 | Triz | 4-OMe | Me | Me | Me | — |
| 1-8 | Triz | 4-Ph | Me | Me | Me | — |
| 1-9 | Triz | 4-OCF$_3$ | Me | Me | Me | — |
| 1-10 | Triz | 4-Et | Me | Me | Me | — |
| 1-11 | Triz | 2,4-diCl | Me | Me | Me | — |
| 1-12 | Triz | 2,4-diF | Me | Me | Me | — |
| 1-13 | Triz | 2-Cl,4-F | Me | Me | Me | — |
| 1-14 | Triz | 2-F,4-Cl | Me | Me | Me | — |
| 1-15 | Triz | 2-OM | Me | Me | Me | — |
| 1-16 | Triz | 2-Cl | Me | Me | Me | — |
| 1-17 | Triz | 2-F | Me | Me | Me | — |
| 1-18 | Triz | 2,6-diCl | Me | Me | Me | — |
| 1-19 | Triz | 2,6-diF | Me | Me | Me | — |
| 1-20 | Triz | 2-Cl,6-F | Me | Me | Me | — |
| 1-21 | Triz | 3-OMe | Me | Me | Me | — |
| 1-22 | Triz | 3-Cl | Me | Me | Me | — |
| 1-23 | Triz | 2,4,6-triCl | Me | Me | Me | — |
| 1-24 | Triz | 2,4,6-triMe | Me | Me | Me | — |
| 1-25 | Triz | 4-iPr | Me | Me | Me | — |
| 1-26 | Triz | 4-Pr | Me | Me | Me | — |
| 1-27 | Triz | 4-Bu | Me | Me | Me | — |
| 1-28 | Triz | 4-OCF$_2$CF$_3$ | Me | Me | Me | — |
| 1-29 | Triz | 3,4-diCl | Me | Me | Me | — |

TABLE 1-continued

| Cpd. No. | A | (X)$_n$ | R$^1$ | R$^2$ | R$^3$ | W |
|---|---|---|---|---|---|---|
| 1-31 | Triz | 3,4-diBr | Me | Me | Me | — |
| 1-32 | Triz | 4-CH$_2$F | Me | Me | Me | — |
| 1-33 | Triz | 4-CHF$_2$ | Me | Me | Me | — |
| 1-34 | Triz | 4-OCH$_2$F | Me | Me | Me | — |
| 1-35 | Triz | 4-OCHF$_2$ | Me | Me | Me | — |
| 1-36 | Triz | 4-OCF$_2$Br | Me | Me | Me | — |
| 1-37 | Triz | 4-CF$_2$Cl | Me | Me | Me | — |
| 1-38 | Triz | 3,5 diCl,4-OCF$_3$ | Me | Me | Me | — |
| 1-39 | Imid | H | Me | Me | Me | — |
| 1-40 | Imid | 4-Cl | Me | Me | Me | — |
| 1-41 | Imid | 4-F | Me | Me | Me | — |
| 1-42 | Imid | 4-Br | Me | Me | Me | — |
| 1-43 | Imid | 4-Me | Me | Me | Me | — |
| 1-44 | Imid | 4-CF | Me | Me | Me | — |
| 1-45 | Imid | 4-OM | Me | Me | Me | — |
| 1-46 | Imid | 4-Ph | Me | Me | Me | — |
| 1-47 | Imid | 4-OCF$_3$ | Me | Me | Me | — |
| 1-48 | Imid | 4-Et | Me | Me | Me | — |
| 1-49 | Imid | 2,4-diCl | Me | Me | Me | — |
| 1-50 | Imid | 2,4-diF | Me | Me | Me | — |
| 1-51 | Imid | 2-Cl,4-F | Me | Me | Me | — |
| 1-52 | Imid | 2-F,4-Cl | Me | Me | Me | — |
| 1-53 | Imid | 2-OMe | Me | Me | Me | — |
| 1-54 | Imid | 2-Cl | Me | Me | Me | — |
| 1-55 | Imid | 2-F | Me | Me | Me | — |
| 1-56 | Imid | 2,6-diCl | Me | Me | Me | — |
| 1-57 | Imid | 2,6-diF | Me | Me | Me | — |
| 1-58 | Imid | 2-Cl,6-F | Me | Me | Me | — |
| 1-59 | Imid | 3-OMe | Me | Me | Me | — |
| 1-60 | Imid | 3-Cl | Me | Me | Me | — |
| 1-61 | Triz | 3-Br | Me | Me | Me | — |
| 1-62 | Triz | 3-Me | Me | Me | Me | — |
| 1-63 | Triz | 2,5-diCl | Me | Me | Me | — |
| 1-64 | Triz | 2,3,4-triCl | Me | Me | Me | — |
| 1-65 | Triz | 2,4,5-triCl | Me | Me | Me | — |
| 1-66 | Triz | 3,4-OCH$_2$O— | Me | Me | Me | — |
| 1-67 | Triz | 4-Cl | Ph | Me | Me | — |
| 1-68 | Triz | 4-F | Ph | Me | Me | — |
| 1-69 | Triz | 4-F | 4-Cl-Ph | Me | Me | — |
| 1-70 | Triz | 4-F | Et | Me | Me | — |
| 1-71 | Triz | 4-F | Pr | Me | Me | — |
| 1-72 | Triz | 4-F | Pr | Me | Me | — |
| 1-73 | Triz | 4-F | Bu | Me | Me | — |
| 1-74 | Triz | 4-F | Me | Me | Me | ½[(COOH)$_2$] |
| 1-75 | Triz | 4-F | Me | Me | Me | HNO$_3$ |
| 1-76 | Triz | 4-F | Me | Me | Me | ½(H$_2$SO$_4$) |
| 1-77 | Triz | 4-F | Me | Me | Me | HCl |
| 1-78 | Triz | 4-F | Me | Me | Me | saccharin |
| 1-79 | Triz | 4-Cl | Me | Me | Me | ½[(COOH)$_2$] |
| 1-80 | Triz | 4-Cl | Me | Me | Me | HNO$_3$ |
| 1-81 | Triz | 4-Cl | Me | Me | Me | ½(H$_2$SO$_4$) |
| 1-82 | Triz | 4-Cl | Me | Me | Me | HCl |
| 1-83 | Triz | 4-Cl | Me | Me | Me | saccharin |
| 1-84 | Imid | 4-F | Me | Me | Me | saccharin |
| 1-85 | Imid | 4-Cl | Me | Me | Me | saccharin |
| 1-86 | Triz | 4-F | Et | Et | Et | — |

TABLE 2

| Cpd. No. | A | (X)$_n$ | R$^1$ | R$^2$ | R$^3$ |
|---|---|---|---|---|---|
| 2-1 | Cl | H | Me | Me | Me |
| 2-2 | Cl | 4-Cl | Me | Me | Me |
| 2-3 | Cl | 4-F | Me | Me | Me |
| 2-4 | Cl | 4-Br | Me | Me | Me |
| 2-5 | Cl | 4-Me | Me | Me | Me |
| 2-6 | Cl | 4-CF$_3$ | Me | Me | Me |
| 2-7 | Cl | 4-OMe | Me | Me | Me |
| 2-8 | Cl | 4-Ph | Me | Me | Me |
| 2-9 | Cl | 4-OCF$_3$ | Me | Me | Me |
| 2-10 | Cl | 4-Et | Me | Me | Me |
| 2-11 | Cl | 2,4-diCl | Me | Me | Me |
| 2-12 | Cl | 2,4-diF | Me | Me | Me |
| 2-13 | Br | 2-Cl,4-F | Me | Me | Me |
| 2-14 | Cl | 2-F,4-Cl | Me | Me | Me |
| 2-15 | Cl | 2-OMe | Me | Me | Me |
| 2-16 | Cl | 2-Cl | Me | Me | Me |

TABLE 2-continued

| Cpd. No. | A | (X)$_n$ | R$^1$ | R$^2$ | R$^3$ |
|---|---|---|---|---|---|
| 2-17 | Cl | 2-F | Me | Me | Me |
| 2-18 | Cl | 2,6-diCl | Me | Me | Me |
| 2-19 | Cl | 2,6-diF | Me | Me | Me |
| 2-20 | Cl | 2-Cl,6-F | Me | Me | Me |
| 2-21 | Br | 3-OMe | Me | Me | Me |
| 2-22 | Cl | 3-Cl | Me | Me | Me |
| 2-23 | Cl | 2,4,6-triCl | Me | Me | Me |
| 2-24 | Cl | 2,4,6-triMe | Me | Me | Me |
| 2-25 | Cl | 4-Pr | Me | Me | Me |
| 2-26 | Cl | 4-Pr | Me | Me | Me |
| 2-27 | Cl | 4-Bu | Me | Me | Me |
| 2-28 | Cl | 4-OCF$_2$CF$_3$ | Me | Me | Me |
| 2-29 | Cl | 3,4-diCl | Me | Me | Me |
| 2-30 | Cl | 3,4-diF | Me | Me | Me |
| 2-31 | Cl | 3,4-diBr | Me | Me | Me |
| 2-32 | Cl | 4-CH$_2$F | Me | Me | Me |
| 2-33 | Cl | 4-CHF$_2$ | Me | Me | Me |
| 2-34 | Cl | 4-OCH$_2$F | Me | Me | Me |
| 2-35 | Cl | 4-OCHF$_2$ | Me | Me | Me |
| 2-36 | Cl | 4-OCF$_2$Br | Me | Me | Me |
| 2-37 | Cl | 4-CF$_2$Cl | Me | Me | Me |
| 2-38 | Cl | 3,5-diCl,4-OCF$_3$ | Me | Me | Me |
| 2-39 | Br | H | Me | Me | Me |
| 2-40 | Br | 4-Cl | Me | Me | Me |
| 2-41 | Br | 4-F | Me | Me | Me |
| 2-42 | Br | 4-Br | Me | Me | Me |
| 2-43 | I | 4-Me | Me | Me | Me |
| 2-44 | Br | 4-CF$_3$ | Me | Me | Me |
| 2-45 | Br | 4-OMe | Me | Me | Me |
| 2-46 | Br | 4-Ph | Me | Me | Me |
| 2-47 | I | 4-OCF$_3$ | Me | Me | Me |
| 2-48 | Br | 4-Et | Me | Me | Me |
| 2-49 | Br | 2,4-diCl | Me | Me | Me |
| 2-50 | Br | 2,4-diF | Me | Me | Me |
| 2-51 | I | 2-Cl,4-F | Me | Me | Me |
| 2-52 | Br | 2-F,4-Cl | Me | Me | Me |
| 2-53 | Br | 2-OMe | Me | Me | Me |
| 2-54 | Br | 2-Cl | Me | Me | Me |
| 2-55 | I | 2-F | Me | Me | Me |
| 2-56 | Br | 2,6-diCl | Me | Me | Me |
| 2-57 | Br | 2,6-diF | Me | Me | Me |
| 2-58 | Br | 2-Cl,6-F | Me | Me | Me |
| 2-59 | I | 3-OMe | Me | Me | Me |
| 2-60 | Br | 3-Cl | Me | Me | Me |
| 2-61 | Br | 3-Br | Me | Me | Me |
| 2-62 | Br | 3-Me | Me | Me | Me |
| 2-63 | Br | 2,5-diCl | Me | Me | Me |
| 2-64 | Br | 2,3,4-triCl | Me | Me | Me |
| 2-65 | Cl | 2,4,5-triCl | Me | Me | Me |
| 2-66 | Br | 3,4-OCH$_2$O— | Me | Me | Me |
| 2-67 | Cl | 4-Cl | Ph | Me | Me |
| 2-68 | Cl | 4-F | Ph | Me | Me |
| 2-69 | Cl | 4-F | 4-Cl-Ph | Me | Me |
| 2-70 | Cl | 4-F | Et | Me | Me |
| 2-71 | Cl | 4-F | Pr | Me | Me |
| 2-72 | Cl | 4-F | Bu | Me | Me |
| 2-73 | Br | 4-Me | Me | Me | Me |
| 2-74 | Br | 2-F | Me | Me | Me |

TABLE 3

| Cpd. No. | (X)$_n$ | R$^1$ | R$^2$ | R$^3$ |
|---|---|---|---|---|
| 3-1 | H | Me | Me | Me |
| 3-2 | 4-Cl | Me | Me | Me |
| 3-3 | 4-F | Me | Me | Me |
| 3-4 | 4-Br | Me | Me | Me |
| 3-5 | 4-CF$_3$ | Me | Me | Me |
| 3-6 | 4-OCF$_3$ | Me | Me | Me |
| 3-7 | 2,4-diCl | Me | Me | Me |
| 3-8 | 2,4-diF | Me | Me | Me |
| 3-9 | 2-Cl,4-F | Me | Me | Me |
| 3-10 | 2-F,4-Cl | Me | Me | Me |
| 3-11 | 2-Cl | Me | Me | Me |
| 3-12 | 2-F | Me | Me | Me |
| 3-13 | 2,6-diCl | Me | Me | Me |
| 3-14 | 2,6-diF | Me | Me | Me |
| 3-15 | 2-Cl,6-F | Me | Me | Me |
| 3-16 | 3-Cl | Me | Me | Me |
| 3-17 | 3,4-diCl | Me | Me | Me |
| 3-18 | 4-OCH$_2$F | Me | Me | Me |
| 3-19 | 4-OCF$_2$H | Me | Me | Me |
| 3-20 | 4-Cl | Et | Me | Me |
| 3-21 | 4-F | Et | Me | Me |
| 3-22 | 4-Br | Et | Me | Me |
| 3-23 | 4-CF$_3$ | Et | Me | Me |
| 3-24 | 4-OCF$_3$ | Et | Me | Me |
| 3-25 | 2,4-diCl | Et | Me | Me |
| 3-26 | 2,4-diF | Et | Me | Me |
| 3-27 | 2-Cl | Et | Me | Me |
| 3-28 | 2-F | Et | Me | Me |
| 3-29 | 2,6-diCl | Et | Me | Me |
| 3-30 | 2,6-diF | Et | Me | Me |
| 3-31 | 4-Me | Me | Me | Me |
| 3-32 | 4-F | Ph | Me | Me |
| 3-33 | 4-F | 4-Cl-Ph | Me | Me |
| 3-34 | 4-F | Pr | Me | Me |
| 3-35 | 4-F | iPr | Me | Me |
| 3-36 | 4-F | Bu | Me | Me |
| 3-37 | 4-Cl | Bu | Me | Me |
| 3-38 | 4-Cl | Et | Et | Et |

Of the compounds listed above, the following are preferred, that is to say Compounds Nos. 1-1, 1-2, 1-3, 1-4, 1-5, 1-6, 1-9, 1-11, 1-12, 1-13, 1-14, 1-15, 1-16, 1-17, 1-18 and 1-19; more preferred compounds are Compound Nos. 1-1, 1-2, 1-3, 1-6, 1-11, 1-12, 1-13 and 1-14; and the most preferred compounds are Compounds Nos.:

1-2. 2-(4-chlorophenyl)-1-(1H-1,2,4-triazol-1-yl)-3-trimethylsilyl-2-propanol;

1-3. 2-(4-fluorophenyl)-1-(1H-1,2,4-triazol-1-yl)-3-trimethylsilyl-2-propanol; and 1-12. 2-(2,4-difluorophenyl)-1-(1H-1,2,4-triazole-1-yl)-3-trimethylsilyl-2-propanol.

The compounds of the present invention can be prepared by a variety of methods, whose general techniques are known in the art for the preparation of compounds of this type. For example, they may be prepared by:

(a) condensing a compound of formula (II):

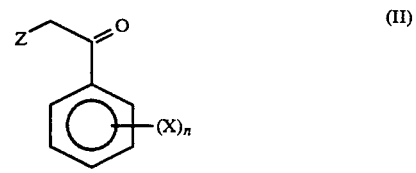

(II)

(wherein X and n are as defined above and Z represents either A or Y, as defined above) with a compound of formula (III):

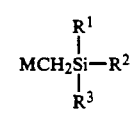

(III)

(wherein R$^1$, R$^2$ and R$^3$ are as defined above, and M represents a lithium atom, a group of formula MgCl or a group of formula MgBr), to give a compound of formula (IV):

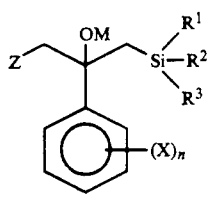 (IV)

(wherein X, n, Z, M, R¹, R² and R³ are as defined above);

(b) removing the atom or group represented by M to give a compound of formula (V):

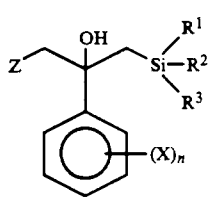 (V)

(wherein X, n, Z, R¹, R² and R³ are as defined above);

(c) optionally, where Z represents Y, reacting said compound of formula (V) with 1,2,4-triazole or imidazole, to give a compound of formula (I);

(d) optionally reacting said compound of formula (IV) or said compound of formula (V) with a base or another cyclising agent, to give said compound of formula (I-3);

(e) optionally salifying any of the products of steps (a), (b) and (c).

In more detail, the compounds of the present invention may be prepared as illustrated in the following Reaction Schemes Reaction Scheme A:

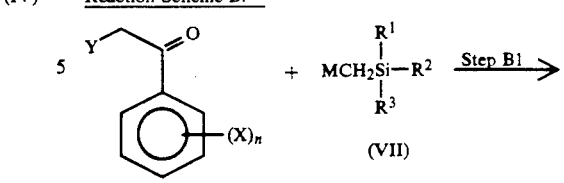

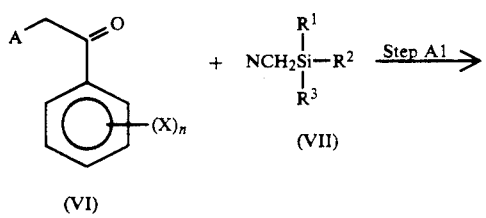

Step A2

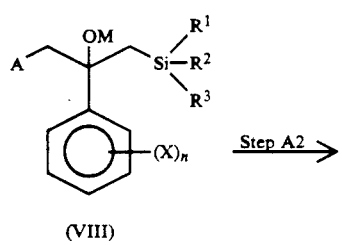

(VIII)

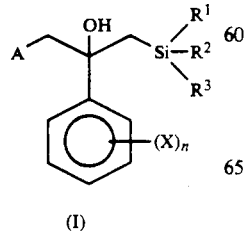

(I)

Reaction Scheme B:

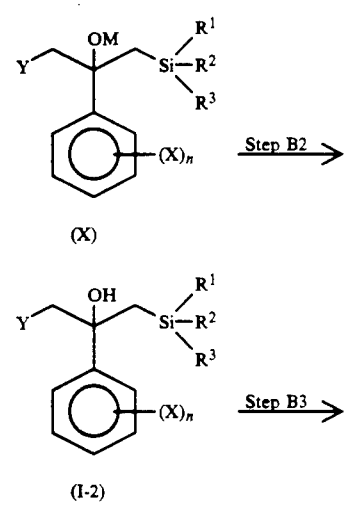

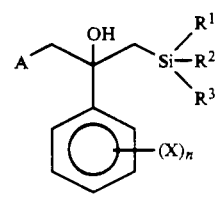

Reaction Scheme C:

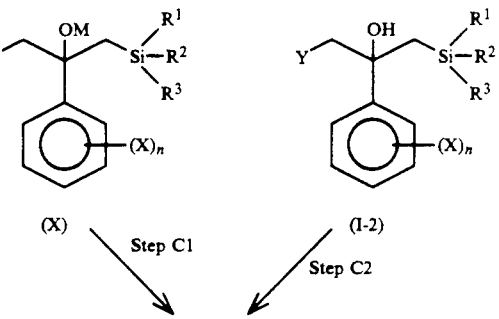

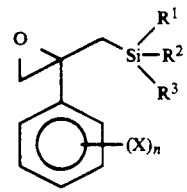 (I-3)

Step C3

Reaction Scheme C:

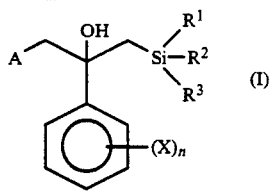

In the above formulae, X, n, Z, M, $R^1$, $R^2$ and $R^3$ are as defined above.

REACTION SCHEME A

Step A1

In this step of Reaction Scheme A, an adduct of formula (VIII) is prepared by the addition of a silyl compound of formula (VII) to a ketone compound of formula (VI).

The ketone compound of formula (VI), which is used as a starting material in this reaction, can be prepared by the method described in Japanese Patent Publication No. Sho 63.46075.

The silyl compound of formula (VII), which is the other starting material in this reaction, can be obtained from a halomethyltrimethylsilyl and metallic magnesium or lithium by conventional means.

The amount of the organic metal silyl compound of formula (VII) employed in this step is preferably from 1 to 10 moles per mole of the ketone compound of formula (VI), more preferably from 1 to 2 moles.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic, cycloaliphatic or aromatic hydrocarbons, such as hexane, cyclohexane, benzene or toluene; halogenated hydrocarbons, especially halogenated aliphatic hydrocarbons, such as methylene chloride, chloroform, dichloroethane or tetrachloroethane; ethers, such as dioxane, diethyl ether, tetrahydrofuran or ethylene glycol dimethyl ether; and amides, such as dimethyl. formamide, dimethylacetamide or hexamethylphosphoric triamide. A single one of these solvents may be used or a mixture of any two or more may be used. Of these solvents, we prefer the ethers.

The reaction can take place over a wide range of temperatures, and the precise reaction temperature is not critical to the invention. In general, we find it convenient to carry out the reaction at a temperature of from $-20°$ C. to $80°$ C., more preferably from $10°$ C. to $40°$ C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 3 hours to 10 hours will usually suffice.

Step A2

In this step, the atom or group represented by M is removed, to liberate a compound of formula (I). The reaction is effected by treating the adduct of formula (VIII) with a weak acid. This is conveniently carried out by dissolving the reaction mixture from Step A1 in water, adding an appropriate amount of a saturated aqueous solution of ammonium chloride, and extracting the reaction mixture with a suitable solvent.

REACTION SCHEME B

Step B1

In this step, an adduct of formula (X) is prepared by the addition of a metal silyl compound of formula (VII) to a ketone compound of formula (IX). The reaction is essentially the same as, and may be carried out in a similar manner to that described in, Step A1 of Reaction Scheme A.

Step B2

In this step, a compound of formula (I-2) is prepared from the adduct of formula (X). The reaction is essentially the same as, and may be carried out in a similar manner to that described in, Step A2 of Reaction Scheme A.

Step B3

In this step, a compound of formula (I) is prepared by reacting the compound of formula (I.2), which may have been prepared as described in step B2, with an excess of 1,2,4-triazole or imidazole in the presence of a base.

The reaction is carried out by reacting the compound of formula (I-2) with at least 1 mole [per mole of the compound of formula (I-2)] of either 1,2,4-triazole or imidazole in a solvent in the presence of at least 1 mole of a base; or by reacting the compound of formula (I-2) with at least 1 mole [per mole of the compound of formula (I-2)] of a salt of either 1,2,4-triazole or imidazole with a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerol, octanol, cyclohexanol or ethylene glycol monomethyl ether; nitro compounds, such as nitroethane or nitrobenzene; nitriles, such as acetonitrile or isobutyronitrile; amides, such as formamide, dimethylformamide, dimethylacetamide, hexamethylphosphoric triamide or 1,3-dimethyl-2-imidazolidinone; and sulfoxides, such as dimethyl sulfoxide or sulfolane. Of these, we prefer the amides, such as formamide, dimethylformamide, dimethylacetamide, hexamethylphosphoric triamide or 1,3 -dimethyl-2-imidazolidinone.

There is likewise no particular limitation on the nature of the base employed, provided that it does not have any adverse effect on any part of the molecule of the compound of formula (I-2), and any base commonly used for conventional reactions of this type may equally be used here. Examples of preferred bases include: alkali metal carbonates, such as sodium carbonate or potassium carbonate; alkali metal hydrogencarbonates, such as sodium hydrogencarbonate or potassium hydrogencarbonate; alkali metal hydrides, such as lithium hydride, sodium hydride or potassium hydride; alkali metal hydroxides, such as sodium hydroxide, potassium hydroxide or barium hydroxide; alkali metal alkoxides, such as sodium methoxide, sodium ethoxide or potassium t-butoxide; organic bases, such as triethylamine, tributylamine, diisopropylethylamine, N-methylmorpholine, pyridine, 4-(N,N-dimethylamino)-pyridine, N,N-dimethylaniline, N,N-diethylaniline, 1,5-diazabicyclo[4.3.0]nona-5-ene, 1,4-diazabicyclo[2.2.2]octane (DABCO) or 1,8-diazabicylo[5.4.0]undec-7-ene (DBU); and organic metal bases, such as butyllithium or lithium diisopropylamide. Of these, we prefer the alkali metal carbonates, such as sodium carbonate or potassium carbonate.

The reaction may be carried out more effectively if it takes place in the presence of one or more of the following compounds: quaternary ammonium salts, such as benzyltriethylammonium chloride or tetrabutylammonium chloride; alkali metal halides, such as sodium iodide, sodium bromide or lithium bromide; crown ethers, such as dibenzo 18-crown6; or molecular sieve 3A or 4A, which may be employed for drying the solvent.

The reaction can take place over a wide range of temperatures, and the precise reaction temperature is not critical to the invention. In general, we find it convenient to carry out the reaction at a temperature of from −78° C. to 200° C., more preferably from −20° C. to 150° C. The time required for the reaction may also vary widely, depending on many factors, notably the reaction temperature and the nature of the reagents and solvent employed. However, provided that the reaction is effected under the preferred conditions outlined above, a period of from 1 hour to 24 hours, more preferably from 2 hours to 10 hours, will usually suffice.

The ketone compound of formula (IX) can be prepared by the method described in Beilsteins Handbuch der Organischen Chemie 7, 285; 7, 283.

REACTION SCHEME C

In this step, a compound of formula (I-3) is prepared by treating the adduct of formula (X), which may have been prepared as described in Step B1, with a suitable chelating reagent to remove the group or atom represented by M and thereby to form an epoxy group. We prefer to employ the adduct of formula (X) in the form of the reaction mixture as obtained from Step B1, without any intermediate isolation.

There is no particular limitation on the nature of the reagent employed to remove the group or atom represented by M, and any reagent known for use in reactions of this type may equally be used here. We prefer to use a highly polar solvent having a chelating ability, and examples of these include: ethers, such as tetrahydrofuran, dioxane, dimethoxyethane or diethylene glycol dimethyl ether; sulfoxides, such as dimethyl sulfoxide or sulfolane; amides, such as formamide, dimethylformamide, dimethylacetamide, hexamethyl. phosphoric triamide or 1,3-dimethyl-2-imidazolidine; ketones, such as acetone, methyl ethyl ketone or methyl isobutyl ketone; and esters, such as methyl acetate, ethyl acetate or propyl acetate. Of these, we prefer the amides, especially dimethylformamide or dimethyl acetamide.

Alternatively, if a crown ether, such as dibenzo-18-crown-6 is present in the reaction mixture, an aromatic hydrocarbon, such as benzene, toluene or xylene, can be employed as the reaction solvent The reaction can take place over a wide range of temperatures, and the precise reaction temperature is not critical to the invention. In general, we find it convenient to carry out the reaction at a temperature of from −50° C. to 50° C., more preferably −20° C. to 30° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably 20 minutes to 2 hours, will usually suffice.

The amount of the chelating reagent used is not particularly limited, provided that it chelates sufficiently with the adduct of formula (X), and the preferred amount may vary depending on the reagent itself and other conditions. For example, where the solvent used for forming the adduct of formula (X) is diethyl ether and the solvent to be added is dimethylformamide, the preferred amount of dimethylformamide is from 1% to 60%, more preferably from 5% to 30%, by volume.

After the addition of the additive, a solvent of low polarity, such as hexane, is added to the reaction mixture, and then water is added, to extract the desired epoxy compound (I-3). This may then be separated and isolate by conventional means from the aqueous extract. If water is added first and hexane extraction is carried out, decomposition of the compound (I-3) occurs.

Step C2

In this step, an epoxide of formula (I-3) is prepared by treating the compound of formula (I.2) with a base.

There is no particular limitation on the nature of the base employed, provided that it does not inhibit the reaction, and any base commonly used in reactions of this type may equally be used here. Examples of preferred bases include alkali metal salts, such as the lithium salt, the sodium salt or the potassium salt of an azole. Examples of azoles which may be employed include imidazole and 1,2,4-triazole. Other preferred bases include alkali metal salts of cyclic secondary amines, such as pyrrolidine, piperidine or morpholine, preferably a sodium salt of pyrrolidine.

There is no particular limitation on the amount of base used, provided that it does not inhibit the reaction; however, in general we prefer that the base should be added in an amount of from 0.8 to 1.5 moles, more preferably from 1 to 1.2 moles, per mole of the compound of formula (I-2).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerol, octanol, cyclohexanol or ethylene glycol monomethyl ether; nitro compounds, such as nitroethane or nitrobenzene; nitriles, such as acetonitrile or isobutyronitrile; amides, such as formamide, dimethylformamide, dimethylacetamide, hexamethylphosphoric triamide or 1,3-dimethyl-2-imidazolidinone; and sulfoxides, such as dimethyl sulfoxide or sulfolane. Of these, we prefer the amides, such as formamide, dimethylformamide, dimethylacetamide, hexamethylphosphoric triamide or 1,3-dimethyl-2-imidazolidinone.

The reaction can take place over a wide range of temperatures, and the precise reaction temperature is not critical to the invention. In general, we find it convenient to carry out the reaction at a temperature of from −78° C. to 200° C., more preferably from −20° C. to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 2 hours, will usually suffice.

After completion of the reaction, the desired compound of formula (I-3) may be extracted in the same manner as described in Step C1, wherein an extraction solvent of low polarity, such as hexane, is added to the reaction mixture, after which water is added thereto to perform extraction and separation.

Step C3

In this step, a compound of formula (I) is prepared by reacting the compound of formula (I-3), which may have been prepared as described in Step C1 or C2, with 1 mole or more of 1,2,4-triazole or imidazole per mole of the compound of formula (I-3), preferably in the presence of 1 mole or more of a base. Alternatively, it may be prepared by reacting the compound of formula (I-3) with a salt of 1,2,4-triazole or imidazole with a base. The reaction is essentially the same as, and may be carried out in a similar manner to that described in, Step B3 of Reaction Scheme B.

We prefer to carry out this Step C3 by reacting the compound of formula (I-3) with an equimolar amount of a salt of 1,2,4-triazole or imidazole with a base together with an equimolar amount of 1,2,4-triazole or imidazole.

After completion of the reaction in each of the above Steps, the reaction product may be collected from the reaction mixture by conventional means. For example, the desired product can be obtained by adding a water-immiscible organic solvent to the reaction mixture, washing the mixture with water, and then removing the solvent, preferably by evaporation. The desired compound thus obtained may be further purified, if necessary, by conventional means, such as recrystallization, reprecipitation or the various chromatography techniques, notably column chromatography.

Salts of the compounds of formula (I) may be prepared by conventional means, preferably simply by adding an acid to a solution of the compound, e.g. a solution prepared by dissolving a condensate of the extract from a reaction mixture containing the compound of formula (I), which may have been prepared as described in any of Reaction Schemes A to C, in an appropriate solvent, or prepared by dissolving the previously isolated compound of formula (I) in an appropriate solvent. The acid employed will, of course, depend on the salt which is to be prepared. By way of example, suitable acids include: inorganic acids, such as the hydrohalic acids (for example hydrofluoric acid, hydrochloric acid, hydrobromic acid or hydroiodic acid), nitric acid, perchloric acid, sulfuric acid or phosphoric acid; organic acids, such as the lower alkylsulfonic acids (for example methanesulfonic acid, trifluoromethansulfonic acid or ethanesulfonic acid), arylsulfonic acids (for example benzenesulfonic acid or p-toluenesulfonic acid), or organic carboxylic acids (for example succinic acid or oxalic acid); and organic acid amide compounds, such as saccharin.

In general, it is best to use the acid in an amount at least equimolar with respect to the compound of formula (I), preferably in an amount of from 1 to 10, more preferably from 1 to 5, moles per mole of the compound of formula (I).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran or dioxane; and alcohols, such as methanol or ethanol.

The reaction can take place over a wide range of temperatures, and the precise reaction temperature is not critical to the invention. In general, we find it convenient to carry out the reaction at a temperature of from −20° C. to 50° C., more preferably from 10° C. to 30° C. The time required for the reaction may also vary widely, depending on many factors, notably the reaction temperature and the nature of the reagents and solvent employed. However, provided that the reaction is effected under the preferred conditions outlined above, a period of from 10 minutes to 1 hour will usually suffice.

The salt formed may be isolated by conventional means. Specifically, where the salt is precipitated as crystals, it may be isolated by filtration, or, when it is a water-soluble salt, it may be isolated as an aqueous solution by separation using an organic solvent and water.

The compounds of the present invention have a variety of valuable biological activities, as shown by the following Experiments, which make them useful as both agricultural and pharmaceutical anti-fungal agents.

In more detail, since the compounds of the present invention show a very high systemic translocation, they may be used not only for foliar application but also for sunmerged application, for which no triazole compound has hitherto been usable in practice. Moreover, they can, in particular, strongly prevent various sclerotial diseases, including sheath blight of rice plants (*Rhizoctonia Sasakii*), and rice blast (*Piricularia oryzae*), which are the main diseases in rice culture.

On the other hand, the use of the compounds of the present invention as fungicides for soil treatment or as fungicides for seed treatment is particularly effective against damping-off of various crops, such as rice, wheat, barley, sugar beet, cotton and other vegetables, and against black scurf (*Corticium vacum*), which are caused by Rhizoctonia spp. Furthermore they can effectively control soil-mediated and seed-mediated infectious diseases, such as Fusarium diseases and Particilium diseases of various crops, eyespot of cereals, damping-off, smut and septoria.

The use of the compounds of the present invention as fungicides for foliar application is, in addition, effective against many kinds of air-mediated infectious diseases, such as powdery mildew, rust and scab.

Crops such as rice, wheat, barley, tomato, potato, cotton, egg-plant, cucumber and kidney bean, are not damaged by the use of the compounds of the present invention at effective and practical doses.

Furthermore, the compounds can also be applied to orchards, non-farm areas, forests and the like. The compounds can also be used as anti-fungal and preservative agents for the treatment of wood.

Reflecting the activity of the compounds of the present invention, the invention further provides compositions which contain one or more of the compounds of the invention, together with a carrier and optionally other auxiliary agents, if necessary. These compositions may be formulated as preparations of the type commonly employed for agricultural or horticultural use, for instance as dusts, coarse dusts, microgranules, fine microgranules, wettable powders, emulsifiable concentrates, aqueous or oily suspensions, and aerosols. It is, of course, not necessary to use a completely pure form of the compound of the invention in the composition and, of course, purification can be suspended at any stage and the resulting crude substance may be used as the active ingredient of the composition.

The carrier employed in such compositions may be natural or synthetic and organic or inorganic; it is generally employed to assist the active ingredient to reach the substrate to be treated, and to make it easier to store, transport or handle the active compound. It may be solid, liquid or gaseous.

Suitable solid carriers include:

inorganic substances, such as clays (examples of which are bentonite, kaolinite, montmorillonite and attapulgite), talc, mica, agalmatolite, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as nut shells (e.g. of walnuts or other nuts), soybean meal, tobacco powder, walnut powder, wheat flour, sawdust, starch and crystalline cellulose; synthetic or natural high molecular weight polymers, especially resins, such as coumarone resins, petroleum resins, alkyd resins, polyvinyl chloride, polyalkylene glycols, ketone resins, ester gums, xanthan gum, copal gum and dammar gum; waxes such as carnauba wax and beeswax; or urea.

Examples of suitable liquid carriers include:

paraffinic or naphthenic hydrocarbons, such as kerosene, mineral oil, spindle oil and white oil; aromatic hydrocarbons, such as benzene, toluene, xylene, solvent naphtha, ethylbenzene, cumene and methylnaphthalene; halogenated hydrocarbons, especially chlorinated hydrocarbons, such as carbon tetrachloride, chloroform, trichloroethylene, monochlorobenzene and o-chlorotoluene; ethers such as dioxane and tetrahydrofuran; ketones, such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, ethanol, isopropanol, hexanol, ethylene glycol, diethylene glycol, cyclohexanol, and benzyl alcohol; ether alcohols, such as ethylene glycol monoethyl ether, ethylene glycol monophenyl ether, diethylene glycol monoethyl ether and diethylene glycol monobutyl ether; other polar solvents, such as dimethylformamide and dimethyl sulfoxide; and water.

Suitable gaseous carriers include:

air, nitrogen, carbon dioxide and fluorocarbon propellants such as those sold under the Trade Mark "Freon"; they may be mixed in a known manner to give a propellant.

The compositions of the invention may contain one or more surface active agents and/or polymers to improve the properties of the compositions and help them to disperse, emulsify, spread, penetrate and bind or to control disintegration, improve fluidity or impart corrosion resistance to the composition, or to stabilize the active compound. Any of the conventional classes of surface active agent (non-ionic, anionic, cationic or amphoteric) may be employed, but it is preferred to employ non ionic and/or anionic surface active agents whereby wetting, adhesion and absorption and desired effects may be improved.

Examples of suitable non-ionic surface active agents include:

the polymerization adducts of ethylene oxide with higher alcohols, such as lauryl alcohol, stearyl alcohol and oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or di- alkylphosphoric acids, such as stearylphosphoric acid or dilauryl phosphoric acid; the polymerization adducts of ethylene oxide with amines, such as dodecylamine; amides or ethoxylated amides of higher fatty acids, such as stearamide; higher fatty acid esters of polyhydric alcohols, such as sorbitan, and the polymerization adducts of ethylene oxide therewith; higher fatty acid esters of glycerol borates or of ethoxylated glycerol borates; glycerides and sucrose esters of fatty acids; and the polymerization adducts of ethylene oxide with propylene oxide.

Examples of suitable anionic surface active agents include:

salts of higher fatty acids, i.e. soaps, e.g. sodium oleate; salts, e.g. sodium and calcium salts, of sulfonic acids and the acids themselves, e.g. ligninsulfonic acid, and aryl sulfonate salts, such as sodium isopropylnaphthalenesulfonate, sodium methylenebisnaphthalenesulfonate, sodium ligninsulfonate or sodium dodecylbenzenesulfonate, or alkyl sulfonate salts, especially sodium dialkyl sulfosuccinates, such as sodium dioctyl sulfosuccinate or sodium 2-ethylhexenesulfonate; salts, e.g. sodium, ammonium and amine salts, of polyoxyethylene alkyl aryl ether sulfates or of polyoxyethylene alkyl ether sulfates or the free acids; or salts of polyoxyethylene alkyl aryl ether phosphates or of polyoxyethylene alkyl phosphates; alkyl sulfate salts, such as sodium lauryl sulfate or oleyl sulfate amine salt;

Examples of suitable cationic surfactants include:

the higher aliphatic amines and ethylene oxide condensates with such amines; quaternary ammonium salts, e.g. chlorides; N-alkylamine acetates; and N-alkylamine oxides;

Examples of amphoteric surfactants include betaines and amino acid type surfactants.

Moreover, the compositions of the present invention may be used in combination with high molecular weight compounds or other formulation agents, in order to assist formulation or to improve biological activity, for example: protective colloids, such as casein, gelatin, gum arabic, albumin, glue, sodium alginate, carboxymethylcellulose, methylcellulose, hydroxyethyl cellulose or polyvinyl alcohol; dispersing agents, such as sodium polyphosphate; inorganic dispersing agents, such as bentonite or veegum; stabilizers; binding agents; and anti-freezing agents. For wider applicability and labor saving, the composition of the invention can, if desired, be combined with one or more other agrochemicals, e.g. fungicides, insecticides, herbicides, plant growth regulators and fertilizers.

The above-mentioned carriers and various auxiliary agents may be used alone or in any desired combination, depending upon the type of preparation, the application and other factors. Similar factors will also be of importance in determining the concentration of the active compound in the formulation.

For example, dusts may conveniently contain from 0.1 to 25% by weight of the active compound, the remainder being a solid carrier.

Wettable powders may conveniently contain, for example, from 1 to 80%, preferably from 25 to 80%, by weight of the compound, the remainder being a solid carrier and a dispersing and wetting agent, if required, together with a protective colloidal agent, a thixotropic agent and an anti-foaming agent.

Granules may conveniently contain from 1 to 35% by weight of the active compound, a major portion of the remainder being a solid carrier. The active compound is homogeneously admixed with the solid carrier or is adhered to or adsorbed onto the carrier surface; the diameter of each granule is preferably from 0.2 to 1.5 mm.

Emulsifiable concentrates may conveniently contain, for example, from 5 to 50% by weight of the active compound and from 5 to 20% by weight of an emulsifying agent, the remainder being a liquid carrier, together with, if required, a corrosion inhibitor.

Oil preparations may conveniently contain from 0.5 to 5% by weight of the active compound, the remainder being a liquid carrier such as kerosene.

Aerosols may conveniently contain from 0.1 to 5% by weight of the active compound and optionally a perfume, the remainder being an oily and/or aqueous carrier, and a propellant such as liquified petroleum gas, a fluorocarbon or carbon dioxide.

The compositions of the invention may be applied, for example, to paddy or other fields before or after emergence of disease in plants or to plants already infected with harmful fungi; a concentration of from 10 to 500 ppm for the active ingredient is usually suitable, especially for application to leaves and stems of plants and to soil, whereby effective control may be attained.

The composition of the invention may conveniently be blended with other fungicide for a broader fungicidal spectrum and, in some case, a synergistic effect may be expected. Suitable other fungicides include:

carbamate-type fungicides;

such as 3,3'-ethylenebis(tetrahydro-4,6-dimethyl-2H-1,3,5-thiadiazine-2-thione, zinc or manganese ethylenebisdithiocarbamate, bis(dimethyldithio carbamoyl)disulfide, zinc propylenebisdithiocarbamate, methyl 1-(butylcarbamoyl)-2-benzimidazolcarbamate, 1,2-bis(3-methoxycarbonyl-2-thioureido)benzene and bisdimethyldithiocarbamoyl zinc ethylenebisdithio carbamate;

dicarboximide-type fungicides;

such as N-trichloromethylthio-4-cyclohexene-1,2-dicarboximide and N-tetrachloroethylthio-4-cyclohexene1,2-dicarboximide;

oxazine-type fungicides;

such as 5,6-dihydro-2-methyl-1,4-oxazine-3-carboxanilide-4,4-dioxide;

naphthoquinone-type fungicides;

such as 2,3-dichloro-1,4-naphthoquinone;

and other fungicides;

such as 3-hydroxy-5-methylisoxazole, 5-ethoxy-3-trichloromethyl-1,2,4-thiadiazole, 2,4-dichloro-6-(o-chloroanilino)-1,3,5-triazine, 2,3-dicyano-1,4-dithioanthraquinone, copper 8-quinolate, polyoxin, validamycin, tetrachloroisophthalonitrile, 2-(1-methylpropyl)-4,6-dinitrophenol β,β-dimethylacrylate, triphenyltin hydroxide, phytomycin, dinitromethylheptylphenyl crotonate, 5-butyl-2-dimethylamino-6-methylpyrimidin-4-ol, 6-(3,5-dichloro-4-methylphenyl)-3-(2H)pyridazinone, 6-(3-bromophenyl)-3-(2H)-pyridazinone, N-(2,6-dimethylphenyl)-N-methoxyacetylalanine methyl ester and bis(8-guanidinooctyl)amine acetate.

The composition of the invention may be blended with insecticides. Suitable insecticides include:

phosphorus-containing insecticides;

such as O,O-diethyl O-(2-isopropyl-4-methyl-6-pyrimidinyl)phosphorothioate, O,O-diethyl S-[2-(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)-phosphorodithioate, O,O-dimethyl S-[2-(ethylthio)ethyl]phosphorodithioate, O,O-dimethyl-1-hydroxy-2,2,2-trichloroethylphosphonate, O,O-diethyl-O-(5-phenyl-3-isoxazolyl)phosphorothioate, O,O-dimethyl-O-(3-methyl-4-methylmercaptophenyl)thiophosphate, O-ethyl-O-p-cyanophenyl phenylphosphonothioate, O,O-dimethyl S-(1,2-dicarboethoxyethyl)phosphorodithioate, 2-chloro-1-(2,4,5-trichlorophenyl)vinyldimethyl phosphate, 2-chloro-1-(2,4-dichlorophenyl)-vinyldimethyl phosphate, O,O-dimethyl O-p-cyanophenyl phosphorothioate, 2,2-dichlorovinyldimethylphosphate, ethyl mercaptophenylacetate O,O-dimethyl phosphorodithioate, S-[(6-chloro-2-oxo-3-benzooxazolinyl)methyl]-O,O-diethylphosphorodithioate, 4-methylthiophenyl dipropylphosphate, 2-chloro-1-(2,4-dichlorophenyl)vinyldiethylphosphate, O,O-diethyl O-(3-oxo-2-phenyl-2H-pyridazin-6-yl)phosphorothioate, O,O-dimethyl S-(1-methyl-2-ethylsulfinyl)ethyl phosphorothioate, O,O-dimethyl S-phthalimidomethyl phosphorodithioate, dimethylmethylcarbamoylethylthioethyl thiophosphorothioate, O,O-diethyl S-(N-ethoxycarbonyl-N-methylcarbamoylmethyl)phosphorodithioate, O,O-dimethyl-S-[2-methoxy-1,3,4-thiadiazol-5(4H)-onyl-(4)-methyl]dithiophosphate, 2-methoxy-4H-1,3,2-benzodioxaphosphorin 2-sulfide, O,O-diethyl-O-(3,5,6-trichloro-2-pyridyl)phosphorothioate, O,S-dimethyl-N-acetyl phosphoroamidothioate, O-2,4-dichlorophenyl O-ethyl S-propylphosphorodithioate, O,O-diethyl S-(2-chloro-1-phthalimidoethyl)phosphorodithioate and O-6-ethoxy-2-ethylpyrimidin-4-yl O,O-dimethylphosphorothioate;

carbamate-type insecticides;

such as 1-naphthyl N-methylcarbamate, S-methyl-N-[methylcarbamoyloxy]thioacetoimidate, 2-sec-butylphenyl-N-methylcarbamate, 2-isopropoxyphenyl-N- methylcarbamate, 1,3-bis(carbamoylthio)-2-(N,N-dimethylamino)propane hydrochloride and 2-dimethylamino-5,6-dimethylphyrimidin-4-yl dimethylcarbamate;

and other insecticides;

such as nicotine sulfate, milbemycin D, 6-methyl-2,3-quinoxalinedithiocyclic S,S-dithiocarbonate, 2,4-dinitro-6-sec-butylphenyldimethylacrylate, 1,1-bis(p-chlorophenyl)-2,2,2-trichloroethanol, azoxybenzene, di(p-chlorophenyl)cyclopropyl carbinol, isopropyl 4,4'-dichlorobenzilate, ethyl 4,4'-dichlorobenzilate, ethyl O-benzoyl-3-chloro-2,6-dimethoxybenzohydroxymate, isopropyl 4,4'-dibromobenzilate, tricyclohexyltin hydroxide, hexakis($\beta,\beta$-dimethylphenethyl)distanoxane, 2-(4-t-butylphenoxy)cyclohexylpropinylsulfide, 3-methyl-1,5-bis(2,4-xylyl)-1,3,5-triazapenta-1,4-diene, 2,4,5,4'-tetrachlorodiphenyl sulfone, hexachlorohexahydromethanobenzodioxathiepine oxide, 5-dimethylamino-1,2,3-trithiane hydrogen oxalate and machine oil.

However, the nature of any such additional insecticide is not critical.

Additionally, if desired, the compounds of the present invention may be blended with other conventional agricultural or horticultural materials, such as acaricides, nematocides, herbicides, plant growth regulators, manure or soil conditioners, to provide compositions having a wider range of applications and/or to reduce labor costs.

The amount of the compound of the present invention used varies depending upon the weather conditions, the type of preparation, the time of application, the method of application, the nature of the environment, the nature of the disease, the nature of the plant and various other known factors, but the compound may preferably be applied in an amount of from 0.1 to 100 g of the effective ingredient per are, preferably from 5 to 40 g. Emulsifiable concentrates, wettable powders, suspension concentrates and the like are preferably applied by diluting a prescribed amount with, for example, from 1 to 10 liters of water per are and granules are generally applied without dilution. If desired, other additives, such as spreaders, e.g. surface active agents, polyoxyethylene resin acid, ligninsulfonates, salts of abietic acid, dinaphthylmethanedisulfonate, paraffin, may be added to the water used for the dilution.

The compounds of the present invention can also be used as pharmaceuticals for the treatment of fungal infections, whether of the skin, in which case they are normally administered topically, or internal infections, in which case they may be administered orally or parenterally. They are thought to be of especial value in the treatment of acute mycosis, such as candidiasis.

Where the compound of the present invention is employed for pharmaceutical use, it may be administered in the form of any conventional pharmaceutical formulation, the nature of which will, as is well known, depend on the route of administration and the nature of the condition to be treated. Thus, the compounds of the invention may be formulated in conventional dosage forms, normally in admixture with a pharmaceutical carrier or diluent. For oral administration, the compounds can be formulated, for example, as tablets, capsules, granules, powders or syrups. For parenteral administration, they may be formulated as injections in a suitable liquid or as suppositories. For topical administration, they may be formulated as ointments, creams, powders, liquids or aerosols. These pharmaceutical preparations can be produced by conventional means using adjuvants generally known in this field, such as excipients, diluents, dispersants, binders, disintegrators, lubricants, stabilizers, corrigents and the like.

The dosage and frequency of administration may vary depending upon the symptoms, age and body weight of the patient, as well as upon the route of administration, but, in general, the compounds of the invention may be administered orally in a daily dose of from 50 to 2,000 mg for an adult, preferably a dosage of from 100 to 600 mg, which may be administered either as single dose or as divided doses.

The activity of the compounds of the present invention is illustrated by the following Experiments.

In these Experiments, the compounds of the present invention are identified by the number of the Example given hereafter which illustrates their preparation and also by the Compound number assigned to them in the foregoing Table 1. Comparative tests were also carried out against a number of prior art compounds, and these prior art compounds are identified as follows:

A: isomer 1 of 4-(4-chlorophenyl)-4-hydroxy-5-(2,3,5-triazol-1-yl)-3-trimethylsilyl-1-pentene, J-F. Chollet et al. [Pestic. Sci., 29, 427–435 (1990)], compound XX;

B: isomer 2 of 4-(4-chlorophenyl)-4-hydroxy-5-(1,2,4-triazol-1-yl)-3-trimethylsilyl-1-pentene, J-F. Chollet et al. [Pestic. Sci., 29, 427–435 (1990)], compound XX;

C: 3-t-butyl-3-hydroxy-4-(1,2,4-triazol-1yl)-1-trimethylsilyl-1-pentyne, GB Patent Specification No. 2 175 301, Example 11, isomer A;

D: 3-(2,4-dichlorophenyl)-3-hydroxy-4-(1,2,4-triazol-1-yl)-1-trimethylsilyl-1-butyne, J. F. Chollet et al. [Pestic. Sci., Sci., 29, 427–435 (1990)], compound II, and an intermediate in Example 4 of GB Patent Specification No. 2 224 278;

E: 4-(4-chlorophenyl)-4-hydroxy-5-(1,2,4-triazol-1-yl)-1-trimethylsilyl-1-pentene, J-F. Chollet et al. [Pestic. Sci., 29 427–435 (1990)], compound XXIII;

F 3-(2,4-dichlorophenyl)-3-hydroxy-4-(1,2,4-triazol-1-yl)-1-trimethylsilyl-1-butene, GB Patent Specification No. 2 224 278, Example 4, compound No. 13.

It should be noted that the two isomers of 4-(4-chlorophenyl)-4-hydroxy-5-(1,2,4.triazol-1-yl)-3-trimethylsilyl-1-pentene, which we have called "compounds A and B", were not separated in the prior art.

EXPERIMENT 1

Curative Activity Against Rice Blast

Rice seedlings (variety "Sachikaze") at the 4–5 leaf stage were inoculated with the fungus *Pyricularia oryzae* by spraying them with a spore suspension of the fungus and maintaining the seedlings in a moist chamber (relative humidity: 100%) at 20–22° C. After 24 hours, the rice seedlings were sprayed with an aqueous suspension of the test compound at a concentration of 10 ppm in an amount of 30 ml per 3 pots. The rice seedlings were then kept in the moist chamber for a further 6 days. As a control, some plants were exposed to the fungus, but were not treated with any anti-fungal agent.

The activity index was determined on the basis of the number of lesions formed on the upper two leaves of each plant. The results are shown in Table 4.

In this Table, the activity index was assigned on the basis of the degree of disease, which was determined by examination with the naked eye and is given by the following codes (the same applies to subsequent Experiments):

5: no disease
4: disease rate was 10% or less of that of the untreated plant
3: disease rate was 10%–30% of that of the untreated plant
2: disease rate was 30%–50% of that of the untreated plant
1: disease rate was 50%–70% of that of the untreated plant
0: disease rate was 70% or more of the untreated plant and almost the same as that of the untreated plant.

EXPERIMENT 2

Preventive Activity Against Sheath Blight of Rice Plants

Rice seedlings (variety Nihonbare) at the 4–5 leaf stage were sprayed with an aqueous suspension of the test compound at a concentration of 100 ppm (30 ml/3 pots). The seedlings were then kept for 24 hours at room temperature, after which they were inoculated with *Rhizoctonia solani* by placing 4–5 oat grains on which the fungus had previously been cultured around the base of each seedling. The seedlings were then kept in a moist chamber (relative humidity: 100%) for 5 days at 25°–27° C. The activity index was given on the basis of the height of the lesions formed on the rice seedlings.

The results are shown in Table 4.

EXPERIMENT 3

Curative Activity Against Sheath Blight of Rice Plants

Rice seedlings (variety Nononbare) at the 4–5 leaf stage were inoculated with *Rhizoctonia solani* by placing 4–5 oat grains on which the fungus had previously been cultured around the base of each rice seedling and keeping them in a moist chamber (relative humidity: 100%) at 25°–27° C. After 24 hours, the rice seedlings were sprayed with an aqueous suspension of the test compound at a concentration of 10 ppm (30 ml/3 pots) and continued to be kept in the moist chamber for a further 5 days. The activity index was given on the basis of the height of the lesions formed on the rice seedlings.

The results are shown in Table 6.

EXPERIMENT 4

Preventive Activity Against Sheath Blight of Rice Plants by Submerged Application Rice seedlings (variety Nihonbare) at the 3–4 leaf stage grown in pots were flooded to a depth of 1 cm with water. The test compound was then applied to the water in the pots in an amount corresponding to 100 g per 10 acres. After the seedlings had been kept in a green-house for 7 days, they were inoculated with *Rhizoctonia solani* by placing 4–5 oat grains on which the fungus had previously been cultured around the base of each seedling. The seedlings were then kept in a moist chamber (relative humidity: 100%) for 5 days at 25°–27° C. The activity index was given on the basis of the height of the lesions formed on the rice seedlings.

The results are shown in Table 4.

EXPERIMENT 5

Curative Activity Against Leaf Rust of Wheat

Wheat seedlings (variety Norin No. 61) at the 1.5 leaf stage were inoculated with the fungus *Puccinia recondita* by sprinkling the spores of the fungus onto the seedlings. They were then kept in a moist chamber (relative humidity: 100%) for 24 hours at 20°–22° C., after which they were moved to a green-house at 15°–20° C. After 2 days, the seedlings were sprayed with an aqueous suspension of the test compound at a concentration of 3 ppm (30 ml/3 pots). The seedlings were then continuously kept in the green-house for 10 days. The activity index was given on the basis of diseased area on the first leaf at the end of this time.

The results are shown in Table 4.

EXPERIMENT 6

Curative Activity Against Powdery Mildew of Barley

Barley seedlings (variety Sekishinriki) at the first leaf stage were inoculated with conidia of *Erysiphe graminis* f. sp. hordei by sprinkling spores of the fungus on the seedlings, which were then kept in a green-house at 15°–20° C. After one day, the seedlings were sprayed with an aqueous suspension of the test compound at a concentration 3 ppm (30 ml/3 pots), and they continued to be kept in the green-house at that temperature for a further 10 days. The activity index was given on the basis of the diseased area on the first leaf at the end of that time.

The results are shown in Table 4.

TABLE 4

| Example No. (Cpd. No.) | Experiment No. | | | | | |
|---|---|---|---|---|---|---|
| | 1 | 2 | 3 | 4 | 5 | 6 |
| 1 (1-1) | 5 | 5 | 5 | 5 | 3 | 5 |
| 2 (1-3) | 5 | 5 | 5 | 5 | 5 | 5 |
| 3 (1-2) | 5 | 5 | 5 | 5 | 5 | 5 |
| 4 (1-4) | 0 | 5 | 5 | — | 5 | 5 |
| 5 (1-5) | 0 | 2 | 3 | 0 | 1 | 5 |
| 7 (1-8) | 0 | 2 | 4 | 0 | 1 | 5 |
| 8 (1-6) | 5 | 2 | 4 | 4 | 5 | 5 |
| 9 (1-7) | 0 | 2 | 4 | 3 | 0 | 2 |
| 11 (1-15) | — | — | — | — | 2 | 5 |
| 12 (1-12) | 5 | 5 | 5 | 4 | — | — |
| 13 (1-11) | 0 | 5 | 5 | 4 | 5 | 5 |
| 14 (1-14) | 5 | 5 | 5 | 5 | 5 | 5 |
| 15 (1-13) | 5 | 5 | 5 | 5 | 5 | 5 |
| 17 (1-29) | 2 | 3 | 3 | 1 | 1 | 4 |
| 23 (1-17) | 2 | 4 | 4 | 4 | 1 | 3 |
| 24 (1-16) | 2 | 4 | 4 | 4 | — | — |
| 25 (1-61) | 1 | 3 | 4 | 0 | 0 | 3 |
| 31 (1-74) | 2 | 4 | 4 | 1 | 3 | 5 |
| 32 (1-75) | 1 | 4 | 4 | 2 | 4 | 5 |
| 33 (1-78) | 3 | 5 | 5 | 1 | 4 | 5 |
| 34 (1-83) | 3 | 5 | 5 | 1 | 4 | 5 |
| 35 (1-67) | 0 | 2 | 2 | 0 | 1 | 4 |
| 36 (1-68) | 0 | 2 | 2 | 0 | 1 | 5 |
| 37 (1-69) | 0 | 3 | 3 | 0 | 1 | 5 |
| 38 (1-70) | 2 | 4 | 4 | 4 | 1 | 5 |
| A | 0 | 1 | 0 | 0 | 1 | 2 |
| B | 0 | 3 | 1 | 3 | 5 | 3 |
| C | 0 | 0 | 1 | 0 | 0 | 0 |
| D | 0 | 0 | 1 | 0 | 4 | 4 |
| E | 0 | 0 | 0 | 0 | 0 | 0 |
| F | 0 | 0 | 3 | 0 | 5 | 3 |

EXPERIMENT 7

Antifungal Activity

A fungal disc of about 4 mm diameter was inoculated on an agar medium (2% by weight malt extract, 1% glucose, 0.3% peptone and 2% agar) in a petri dish of diameter 9 cm, by placing the disc on the center of the medium. Paper disc specimens were prepared by impregnating 30 μl of an acetone solution containing 300 ppm of the test compound into the disc (diameter 8 mm, thickness 0.7 mm) and then subjecting it to dry sterilization. The disc specimens were placed in a circle at about 1 cm distance from the fringe of the grown fungus, three days after the inoculation. The specimens were then maintained at 25° C. for 5 days, after which the antifungal activity was determined by visual observation of infection of the specimens by the fungus. The fungi tested were:

*Aspergillus niger* (Fungus A),
*Gliocladium virens* (Fungus B), and
*Fusarium moliniforme* (Fungus C).

The antifungal activity is indicated by the following ratings:

+: no growth of fungus on the specimens observed
−: growth of fungus on the specimens observed.

The results are shown in the following Table 5.

EXPERIMENT 8

Wood-preservative Activity

The procedure described in Experiment 7 was repeated, except that the fungi tested were *Coriolus versicolor* (Fungus D) and *Tyromyces palustris* (Fungus E), which are prescribed in JIS A-9201. The results are shown in the following Table 5.

TABLE 5

| Example No. (Cpd. No.) | Experiment 7 (Antifungal) | | | Experiment 8 (Antidecay) | |
|---|---|---|---|---|---|
| | Fungus A | Fungus B | Fungus C | Fungus D | Fungus E |
| 1 (1-1) | + | − | + | + | + |
| 2 (1-3) | + | + | + | + | + |
| 3 (1-2) | + | + | + | + | + |
| 4 (1-4) | + | + | + | + | + |
| 5 (1-5) | + | + | + | + | + |
| 8 (1-6) | + | − | + | + | + |
| 12 (1-12) | − | + | + | + | + |
| 13 (1-11) | + | + | + | + | + |
| 14 (1-14) | + | + | + | + | + |
| 17 (1-29) | − | − | + | − | − |
| 18 (1-50) | − | − | + | + | − |
| 21 (1-49) | − | − | − | + | − |
| 23 (1-17) | + | + | + | + | + |
| 24 (1 16) | + | + | + | + | + |
| 28 (1-64) | − | − | − | − | + |
| 29 (1-65) | − | − | + | − | − |
| 33 (1-78) | − | + | + | + | + |
| 34 (1-83) | − | + | + | + | + |
| 37 (1-69) | − | − | + | + | − |
| 38 (1-70) | − | + | + | + | + |

EXPERIMENT 9

Antifungal Test (i) Preparation of the test solution: The sample to be tested was examined to determine a suitable solvent from those listed below and the method of dissolution, and then the sample was weighed (about 10 mg), dissolved in the selected solvent and diluted with sterilized distilled water to a concentration of 500 μg/ml. Samples of the resulting solution were then subjected to sequential dilution to half the previous concentration to prepare 12 samples in which the concentration of active compound is progressively halved.

| Solvent | Maximum concentration employable |
|---|---|
| 1) Sterilized distilled water | |
| 2) 3% Sodium bicarbonate solution | 10% |
| 3) Acetone | 50% |
| 4) N,N-Dimethylformamide (DMF) | 30% |
| 5) Dimethyl sulfoxide (DMSO) | 20% |

(ii) Test procedure for antifungal activity: Using Nunklon (Registered trademark) 24.hole plates (manufactured by Nunk K. K.), 0.1 ml each of the diluted solutions described above was poured into a hole, 0.9 ml of Sabouraud's agar medium was added to each hole, giving a total of 1 ml in each hole, and mixed to prepare the plate medium.

The following 8 strains were employed for the test.

A) Yeast
1 *Candida Albicans* Sc. (*C. albica*)
2 *Candida albicans* 427 (*C. alb* 427)
3 *Cryptococcus neoformans* 58063 (*C. neofor*)

B) Mold
4 *Mucor mucedo* (*M. mucedo*)
5 *Aspergillus fumigatus* (*A. fumiga*)
6 *Microsporum gypseum* (*M. gypseu*)
7 *Trichophyton mentagrophytes* Sc. (*T. mentag*)
8 *Trichophyton rubrum* Sc. (*T. rubrum*)

These test strains were inoculated by means of a slant on Sabouraud's agar medium, cultured at 27° C. for 2 days for the yeast strains or for 7 to 14 days for the mold strains, and, kept intact, preserved at 5° C. (subcultured every 1 month). On the day of the test, in the case of the yeast medium, physiological saline to which had previously been added Tween 80 in an amount of 0.1% (w/v) was added to each medium to prepare $10^6$ cells/ml suspensions; and, in the case of the mold medium, 4 ml each of the solution above was added to the surface of the agar slant, the surface was rubbed slightly with a stirrer or a platinum loop to suspend the spores, and then, by filtration through a funnel on which 2 sterilized gauzes were placed one upon another, $10^6$ cells/ml suspensions were prepared. Using an Eppendorf pipette, 0.1 ml each of these suspension preparations was inoculated and cultivated. The culture was conducted at 27° C. for 2 days for the three strains of yeast, for 5 days for molds 4, 5 and 6, and for 7 days for molds 7 and 8 to determine minimal inhibitory concentrations of the test samples.

The results are shown in Table 6.

TABLE 6

| | MIC (μg/ml) | | |
|---|---|---|---|
| Fungi | Example 2 (Cpd. 1-3) | Example 3 (Cpd. 1-2) | Example 12 (Cpd. 1-12) |
| 1 C. albica | >50 | >50 | >50 |
| 2 C. alb 427 | >50 | >50 | >50 |
| 3 C. neofor | >50 | 12.5 | 6.2 |
| 4 M. mucedo | >50 | >50 | 12.5 |
| 5 A. fumiga | >50 | >50 | 12.5 |
| 6 M. gypseu | >50 | >50 | 1.5 |
| 7 T. mentag | 25 | 3.1 | 0.8 |
| 8 T. rubrum | 25 | 3.1 | 0.8 |

PREPARATIVE EXAMPLES

Example 1

2-Phenyl-1-(1H-1,2,4-triazol-1-yl)-3-trimethylsilyl-2-propanol (Compound No. 1-1)

0.505 g (2.7 mmole) of 2-(1H-1,2,4-triazol-1-yl)-acetophenone was added to 50 ml of diethyl ether. The solution was then stirred at room temperature under a stream of nitrogen, and 13.5 ml (13.5 mmole) of a 1 M tetrahydrofuran solution of trimethylsilylmethylmagnesium chloride were added dropwise at such a rate that the temperature of the reaction mixture did not rise higher than 25° C. After the addition was complete, the reaction mixture was stirred for 30 minutes at room temperature; it was then heated under reflux for 6 hours. At the end of this time, the reaction mixture was cooled, and it was then poured into 100 ml of ice-water. Its pH was adjusted to a value of 6 by the addition of 5% w/v aqueous hydrochloric acid, after which it was extracted three times, each time with 50 ml of ethyl acetate. The organic layers were collected, washed three times, each time with a saturated aqueous solution of sodium chloride and dried over anhydrous sodium sulfate, and then the solvent was removed by distillation under reduced pressure, to afford a crude oily product. 0.112 g (yield 15%) of the title compound, melting at 86°–87° C., was obtained from this crude oily product by purification through a silica gel chromatography column, eluted with mixtures of ethyl acetate and hexane ranging from 1:1 to 2:1 by volume.

Nuclear Magnetic Resonance Spectrum (CDCl$_3$) δ ppm: −0.20 (9H, singlet); 1.20 (1H, doublet, J=14.5 Hz); 1.41 (1H, doublet, J=14.5 Hz); 4.48 (1H, doublet, J=14.8 Hz); 4.58 (1H, doublet, J=14.8 Hz); 7.35–7.24 (5H, multiplet); 7.97 (1H, singlet); 8.59 (1H, singlet).

Mass spectrum (m/z): 276 (M+), 260, 193.

Example 2

2-(4-Fluorophenyl)-1-(1H-1,2,4-triazol-1-yl)-3-trimethylsilyl-2-propanol (Compound No. 1-3)

1.62 g (0.04 mole) of a 60% w/v dispersion of sodium hydride in mineral oil were added to 60 ml of dimethylformamide. Whilst the mixture was being stirred in an ice bath, 2.91 g (0.04 mole) of 1,2,4-triazole were added, and the mixture was stirred for a further 30 minutes at room temperature. At the end of this time, 5.5 g (0.021 mole) of 1 chloro-2-(4-fluorophenyl)-3-trimethylsilyl-2-propanol (prepared as described in Example 40) were added to the reaction mixture, which was then heated for 30 minutes at 90° C. whilst stirring. The reaction mixture was cooled and then poured into 200 ml of ice-water, and the resulting mixture was extracted with 300 ml of ethyl acetate. The organic extract was washed three times, each time with 100 ml of a saturated aqueous solution of sodium chloride. It was then dried over anhydrous sodium sulfate, and the solvent was removed by distillation under reduced pressure, to afford a crude oily product. 2.9 g (yield 47%) of the title compound, melting at 118 119° C., were obtained by purification of this crude oily product by silica gel column chromatography, using mixtures of ethyl acetate and hexane in proportions of 1:5, 1:1 and 2:1 as the eluent.

Nuclear Magnetic Resonance Spectrum (CDCl$_3$) δ ppm: −0.18 (9H, singlet); 1.16 (1H, doublet, J=14.5 Hz); 1.33 (1H, doublet, J=14.5 Hz); 4.36 (1H, doublet, J=14.0 Hz); 4.43 (1H, doublet, J=14.0 Hz); 6.93–7.01 (2H, multiplet); 7.26–7.31 (2H, multiplet); 7.91 (1H, singlet); 7.99 (1H, singlet).

Mass spectrum (m/z): 293 (M+), 278, 211.

EXAMPLES 3 TO 30

The following compounds were obtained by following a similar procedure to that described in Example 1 or Example 2.

Example 3

2-(4-Chlorophenyl)-1-(1H-1,2,4-triazol-1-yl)-3-trimethylsilyl-2-propanol (Compound No. 1-2)

20 mg, yield 7%.

melting at 108°–110° C.

Nuclear Magnetic Resonance Spectrum (CDCl$_3$) δ ppm: −0.19 (9H, singlet); 1.15 (1H, doublet, J=14.5 Hz); 1.31 (1H, doublet, J=14.5 Hz); 4.35 (2H, singlet); 7.17–7.33 (4H, multiplet); 7.80 (1H, singlet); 7.88 (1H, singlet).

Mass spectrum (m/z): 309 (M+), 294, 227, 211.

Example 4

2-(4-Bromophenyl)-1-(1H-1,2,4-triazol-1-yl)-3-trimethylsilyl-2-propanol (Compound No. 1-4)

75 mg, yield 11%.

melting at 120°–121° C.

Nuclear Magnetic Resonance Spectrum (CDCl$_3$) δ ppm: −0.18 (9H, singlet); 120 (1H, doublet, J=14.5 Hz); 1.35 (1H, doublet, J=14.5 Hz); 4.43 (1H, doublet, J=13.9 Hz); 4.51 (1H, doublet, J=13.9 Hz); 7.25 (2H, doublet, J=8.1 Hz); 7.41 (1H, doublet, J=8.1 Hz); 7.96 (1H, singlet); 8.50 (1H, singlet).

Mass spectrum (m/z): 353 (M+), 273, 257.

Example 5

2-(4-Methylphenyl)-1-(1H-1,2,4-triazol-1-yl)-3-trimethylsilyl-2-propanol (Compound No. 1-5)

10 mg, yield 4%.

melting at 101° C.

Nuclear Magnetic Resonance Spectrum (CDCl$_3$) δ ppm: −0.19 (9H, singlet); 1.15 (1H, doublet, J=14.4 Hz); 1.36 (1H, doublet, J=14.4 Hz); 2.30 (3H, singlet); 4.35 (1H, doublet, J=14.0 Hz); 4.43 (1H, doublet, J=14.0 Hz); 7.07 (2H, doublet of doublets, J=8.3 and 1.8 Hz); 7.18 (2H, doublet of doublets, J=8.3 and 1.8 Hz); 7.90 (2H, singlet).

Mass spectrum (m/z): 289 (M+), 274, 256, 207.

Example 6

2-(4-Ethylphenyl)-1(1H-1,2,4-triazol-1-yl)-3-trimethylsilyl-2-propanol (Compound No. 1-10)

13.7 mg, yield 4.0%.

melting at 80 81° C.

Nuclear Magnetic Resonance Spectrum (CDCl$_3$) δ ppm: −0.16 (9H, singlet); 1.23 (3H, triplet, J=7.6 Hz); 1.74 (1H, doublet, J=14.1 Hz); 1.95 (1H, doublet, J=14.1 Hz); 2.64 (2H, quartet, J=7.6 Hz); 4.11 (1H, doublet, J=12.1 Hz); 4.38 (1H, doublet, J=12.1 Hz); 7.05 (2H, doublet of doublets, J=8.5 and 2.0 Hz); 7.90 (2H, doublet of doublets, J=8.5 and 2.0 Hz); 8.11 (1H, singlet): 8.48 (1H, singlet).

mass spectrum (m/z): 303 (M+), 272, 131.

Example 7

2-(4-Biphenylyl)-1-(1H-1,2,4-triazol-1-yl)-3-trimethylsilyl-2-propanol (Compound No. 1-8)

74.7 mg, yield 16%.
melting at 97°–100° C.
Nuclear Magnetic Resonance Spectrum (CDCl$_3$) δ ppm: −0.17 (9H, singlet); 1.20 (1H, doublet, J=14.6 Hz); 1.42 (1H, doublet, J=14.6 Hz); 4.50 (2H, singlet); 7.33–7.62 (9H, multiplet); 7.96 (1H, singlet); 8.34 (1H, singlet).
Mass spectrum (m/z): 351 (M+), 269, 179.

Example 8

1-(1H-1,2,4-Triazol-1-yl)-2-(4-trifluoromethylphenyl)-3-trimethylsilyl-2-propanol (Compound No. 1-6)

26 mg, yield 8%.
melting at 144° C.
Nuclear Magnetic Resonance Spectrum (CDC$_3$) δ ppm: −0.19 (9H, singlet); 1.20 (1H, triplet, J=14.5 Hz); 1.34 (1H, doublet, J=14.5 Hz); 4.44 (1H, doublet, J=14.8 Hz); 4.45 (1H, doublet, J=14.8 Hz); 7.93 (1H, singlet); 8.10 (1H, singlet).
Mass spectrum (m/z): 344 (M+1)+, 328, 261, 234, 171.

Example 9

2-(4-Methoxyphenyl)-1-(1H-1,2,4-triazol-1-yl)-3-trimethylsilyl-2-propanol (Compound No. 1-7)

22 mg, yield 13%.
melting at 85°–87° C.
Nuclear Magnetic Resonance Spectrum (CDCl$_3$) δ ppm: −0.14 (9H, singlet); 1.72 (1H, doublet, J=14.5 Hz); 1.93 (1H, doublet, J=14.5 Hz); 3.81 (3H, singlet); 4.11 (1H, doublet, J=11.9 Hz); 4.33 (1H, doublet, J=11.9 Hz); 6.88 (2H, doublet of doublets, J=9.0 and 2.2 Hz); 7.08 (2H, doublet of doublets, J=9.0 and 2.2 Hz); 8.01 (1H, singlet); 8.19 (1H, singlet).
Mass spectrum (m/z): 305 (M+), 290, 274, 133.

Example 10

2-(3-Methoxyphenyl)-1-(1H-1,2,4-triazol-1-yl)-3-trimethylsilyl-2-propanol (Compound No. 1-21)

112 mg, yield 12%.
melting at 91°–92° C.
Nuclear Magnetic Resonance Spectrum (CDCl$_3$) δ ppm: −0.17 (9H, singlet); 1.15 (1H, doublet, J=14.4 Hz); 1.25 (1H, doublet, J=14.4 Hz); 3.77 (3H, singlet); 4.39 (2H, singlet); 6.78 (1H, multiplet); 6.86 (2H, multiplet); 7.22 (1H, multiplet); 7.84 (1H, singlet); 7.89 (1H, singlet).
Mass spectrum (m/z): 305 (M+), 290, 275, 221.

Example 11

2-(2-Methoxyphenyl)-1-(1H-1,2,4-triazol-1-yl)-3-trimethylsilyl-2-propanol (Compound No. 1-15)

64 mg, yield 12%.
melting at 135°–136° C.
Nuclear Magnetic Resonance Spectrum (CDCl$_3$) δ ppm: −0.197 (9H, singlet); 1.78 (1H, doublet, J=14.1 Hz); 2.26 (1H, doublet, J=14.1 Hz); 3.60 (3H, singlet); 4.02 (1H, doublet, J=11.7 Hz); 4.56 (1H, doublet, J=11.7 Hz); 6.85–7.02 (2H, multiplet); 7.14–7.33 (2H, multiplet); 7.92 (1H, singlet); 8.25 (1H, singlet).
Mass spectrum (m/z): 305 (M+), 290, 275, 221.

Example 12

2-(2,4-Difluorophenyl)-1-(1H-1,2,4-triazole-1-yl)-3-trimethylsilyl-2-propanol (Compound No. 1-12)

742 mg, yield 26.5%.
melting at 112°–114° C.
Nuclear Magnetic Resonance Spectrum (CDCl$_3$) δ ppm: −0.17 (9H, singlet); 1.23 (1H, doublet, J=14.5 Hz); 1.48 (1H, doublet of doublets, J=14.5 and 2.0 Hz); 4.41 (1H, doublet, J=13.7 Hz); 4.43 4.72 (1H, broad); 4.69 (1H, doublet, J=13.7 Hz); 6.69–6.79 (2H, multiplet); 7.40–7.49 (1H, multiplet); 7.83 (1H, singlet); 7.87 (1H, singlet)
Mass spectrum (m/z): 312 (M+1)+, 296, 229.

Example 13

2-(2,4-Dichlorophenyl)-1-(1H-1,2,4-triazol-1-yl)-3-trimethysilyl-2-propanol (Compound No. 1-11)

35 mg, yield 4.1%.
melting at 136°–137° C.
Nuclear Magnetic Resonance Spectrum (CDCl$_3$) δ ppm: −0.10 (9H, singlet); 1.36 (1H, doublet, J=14.5 Hz); 2.04 (1H, doublet, J=14.5 Hz); 4.60 (1H, doublet, J=14.0 Hz); 5.38 (1H, doublet, J=14.0 Hz); 7.30 (1H, doublet of doublets, J=8.1 and 2.1 Hz); 7.42–7.5 (1H, multiplet); 7.78 (1H, doublet, J=8.1 Hz); 7.98 (1H, singlet); 8.04 (1H, singlet)
Mass spectrum (m/z): 344 (M+), 326, 261, 214.

Example 14

2-(4-Chloro-2-fluorophenyl)-1-(1H-1,2,4-triazol-1-yl)-3-trimethylsilyl-2-propanol (Compound No. 1-14)

19 mg, yield 6%.
melting at 129°–130° C.
Nuclear Magnetic Resonance Spectrum (CDCl$_3$) δ ppm:
−0.164 (9H, singlet); 1.20 (1H, doublet, J=14.6 Hz); 1.50 (1H, doublet of doublets, J=14.6 and 1.9 Hz); 4.48 (1H, doublet, J=13.7 Hz); 4.74 (1H, doublet, J=13.8 Hz); 4.51–4.77 (1H, broad); 6.99–7.05 (2H, multiplet); 7.37–7.45 (1H, multiplet); 7.87 (1H, singlet); 8.21 (1H, singlet).
Mass spectrum (m/z): 327 (M+), 312, 245, 155.

Example 15

2-(2-Chloro-4-fluorophenyl)-1-(1H-1,2,4-triazol-1-yl)-3-trimethylsilyl-2-propanol (Compound No. 1-13)

40 mg, yield 5%.
melting at 139°–140° C.
Nuclear Magnetic Resonance Spectrum (CDCl$_3$) δ ppm: −0.17 (9H, singlet); 1.20 (1H, doublet, J=14.6 Hz); 2.04 (1H, doublet, J=14.6 Hz); 4.53 (1H, doublet, J=14.0 Hz); 5.34 (1H, doublet, J=14.0 Hz); 6.87 (1H, doubled doublet of doublets, J=9.0, 8.2 and 6.3 Hz); 7.06 (1H, doublet of doublets, J=8.2 and 2.7 Hz); 7.65 (1H, doublet of doublets, J=9.0 and 6.3 Hz); 7.86 (1H, singlet); 8.23 (1H, singlet).
Mass spectrum (m/z): 327 (M+), 312, 245, 155.

Example 16

2-(4-Fluorophenyl)-1-(1H-1,3-imidazol-1-yl)-3-trimethylsilyl-2-propanol (Compound No. 1-41)

15 mg, yield 5%.
Amorphous.
Nuclear Magnetic Resonance Spectrum (CDCl$_3$) δ ppm: −0.18 (9H, singlet); 1.21 (1H, doublet, J=16.1

Hz); 1.42 (1H, doublet, J=16.1 Hz); 3.95 (2H, broad singlet); 6.95-7.05 (2H, multiplet); 7.12 (2H, singlet); 7.25-7 35 (2H, multiplet); 7.72 (1H, singlet)

Mass spectrum (m/z): 293 (M+1)+, 277, 211, 203.

Example 17

2-(3,4-Dichlorophenyl)-1-(1H-1,2,4-triazol-1-yl)-3-trimethylsilyl-2-propanol (Compound No. 1-29)

180 mg, yield 27%.
melting at 127°-128° C.
Mass spectrum (m/z): 343, 328, 261, 24 , 171.

Example 18

2-(2,4-Difluorophenyl)-1-(1H-1,3-imidazol-1-yl)-3-trimethylsilyl-2-propanol (Compound No. 1-50)

140 mg, yield 97%.
melting at 147°-148° C.
Nuclear Magnetic Resonance Spectrum (CDCl$_3$) δ ppm: −0.19 (9H, singlet); 1.12 (1H, doublet, J=15.0 Hz); 1.64 (1H, doublet, J=15.0 Hz); 4.19 (1H, doublet, J=14.2 Hz); 4.31 (1H, doublet, J=14.2 Hz); 6.72-6.89 (4H, multiplet); 7.38-7.50 (2H, multiplet).
Mass spectrum (m/z): 310, 295, 229, 139.

Example 19

2-Phenyl-1-(1H-1,3-imidazol-1-yl)-3-trimethylsilyl-2-propanol (Compound No. 1-39)

512 mg, yield 93%.
melting at 154°-156° C.
Nuclear Magnetic Resonance Spectrum (CDCl$_3$) δ ppm: −0.195 (9H, singlet); 1.19 (1H, doublet, J=14.7 Hz); 1.42 (1H, doublet, J=14.7 Hz); 4.09 (1H, doublet, J=14.0 Hz); 4.17 (1H, doublet, J=14.0 Hz); 6.63 (1H, singlet); 6.90 (1H, singlet); 7.23 (1H, singlet); 7.29-7.35 (5H, multiplet)
Mass spectrum (m/z) 275, 259, 193, 185, 103.

Example 20

2-(4-Chlorophenyl)-1-(1H-1,3-imidazol-1-yl)-3-trimethylsilyl-2-propanol (Compound No. 1-40)

522 mg, yield 84%.
melting at 173°-174° C.
Nuclear Magnetic Resonance Spectrum (CDCl$_3$) δ ppm: −0.173 (9H, singlet); 1.19 (1H, doublet, J=14.8 Hz); 1.39 (1H, doublet, J=14.8 Hz); 4.09 (2H, singlet); 6.66 (1H, singlet); 6.92 (1H, singlet); 7.25 (1H, singlet); 7.29-7 35 (4H, multiplet).
Mass spectrum (m/z): 309, 293, 227, 219, 137.

Example 21

2-(2,4-Dichlorophenyl)-1-(1H-1,3-imidazol-1-yl)-3-trimethylsilyl-2-propanol (Compound No. 1-49)

408 mg, yield 59%.
melting at 154°-156° C.
Nuclear Magnetic Resonance Spectrum (CDCl$_3$) δ ppm: −0.177 (9H, singlet); 1.08 (1H, doublet, J=15.1 Hz); 2.12 (1H, doublet, J=15.1 Hz); 4.30 (1H, doublet, J=14.3 Hz); 4.64 (1H, doublet, J=14.3 Hz); 6.74 (1H, singlet); 6.89 (1H, singlet); 7.21 (1H, doublet of doublets, J=2.2 and 8.6 Hz); 7.34 (1H, singlet) 7.40 (1H, doublet, J=2.2 Hz); 7.63 (1H, doublet, J=8.6 Hz).
Mass spectrum (m/z): 343, 327, 253.

Example 22

1-(1H-1,3-Imidazol-1-yl)-2-(4-methylphenyl)-3-trimethylsilyl-2-propanol (Compound No. 1-43)

515 mg, yield 89%.
melting at 172°-173° C.
Nuclear Magnetic Resonance Spectrum (CDCl$_3$) δ ppm: −0.186 (9H, singlet); 1.17 (1H, doublet, J=14.7 Hz); 1.41 (1H, doublet, J=14.7 Hz); 2.34 (3H, singlet); 4.06 (1H, doublet, J=15.0 Hz); 4.14 (1H, doublet, J=15.0 Hz); 6.67 (1H, singlet); 6.93 (IH, singlet); 7.22-7.11 (5H, multiplet).
Mass spectrum (m/z): 288, 273, 207, 199, 117.

Example 23

2-(2-Fluorophenyl)-1-(1H-1,2,4-triazol-1-yl)-3-trimethylsilyl-2-propanol (Compound No. 1-17)

44 mg, yield 20%.
melting at 97°-98° C.
Nuclear Magnetic Resonance Spectrum (CDCl$_3$) δ ppm: −0.18 (9H, singlet); 1.19 (1H, doublet, J=14.4 Hz); 1.52 (1H, doublet of doublets, J=14.4 and 1.7 Hz); 4.43 (1H, doublet, J=13.7 Hz); 4.49 (1H, doublet, J=1.7 Hz); 4.76 (1H, doublet, J=13.7 Hz); 6.92-7.06 (2H, multiplet); 7.15-7.21 (1H, multiplet); 7.41-7 45 (1H, multiplet); 7.81 (1H, singlet); 7.82 (1H, singlet).
Mass spectrum (m/z): 293, 278 , 211.

Example 24

2-(2-Chlorophenyl)-1-(1H-1,2,4-triazol-1-yl)-3-trimethylsilyl-2-propanol (Compound No. 1-16)

3.8 mg, yield 2.3%.
melting at 109°-111° C.
Nuclear Magnetic Resonance Spectrum (CDCl$_3$) δ ppm: −0.18 (9H, singlet); 1.21 (1H, doublet, J=14.6 Hz); 1.93 (1H, doublet of doublets, J=14.6 and 1.9 Hz); 4.46 (1H, doublet, J=13.9 Hz); 4.65 (1H, doublet, J=1.9 Hz); 5.28 (1H, doublet, J=13.9 Hz); 7.11-7.16 (2H, multiplet); 7.26-7.31 (1H, multiplet); 7.62-7.67 (IH, multiplet); 7.80 (1H, singlet); 7.84 (1H, singlet).
Mass spectrum (m/z): 309, 294, 227, 137.

EXAMPLE 25

2-(3-Bromophenyl)-1-(1H-1,2,4-triazol-1-yl)-3-trimethylsilyl-2-propanol (Compound No. 1-61)

345 mg, yield 49%.
melting at 90°-91° C.
Nuclear Magnetic Resonance Spectrum (CDCl$_3$) δ ppm: −0.17 (9H, singlet); 1.13 (1H, doublet, J=14.5 Hz); 1.30 (1H, doublet, J=14.5 Hz); 4.23 (1H, singlet); 4.36 (2H, singlet); 7.15-7.38 (3H, multiplet); 7.51-7.53 (1H, multiplet); 7.78 (1H, singlet); 7.91 (1H, singlet).
Mass spectrum (m/z): 353, 340, 271, 181.

Example 26

2-(3-Methylphenyl)-1-(1H-1,2,4-triazol-1-yl)-3-trimethylsilyl-2-propanol (Compound No. 1-62)

60 mg, yield 13%.
melting at 106°-109° C.
Nuclear Magnetic Resonance Spectrum (CDCl$_3$) δ ppm: −0.19 (9H, singlet); 1.12 (1H, doublet, J=14.5 Hz); 1.34 (1H, doublet, J=14.5 Hz); 2.31 (3H, singlet); 3.94 (1H, singlet); 4.37 (2H, singlet); 6.99-7.14 (4H, multiplet); 7.72 (1H, singlet); 7.89 (1H, singlet).
Mass spectrum (m/z): 289, 274, 207, 117.

Example 27

2-(2,5-Dichlorophenyl)-1-(1H-1,2,4-triazol-1-yl)-3-trimethylsilyl-2-propanol (Compound No. 1-63)

7.2 mg, yield 2.7%.
melting at 105°-107° C.
Nuclear Magnetic Resonance Spectrum (CDCl$_3$) δ ppm: −0.14 (9H, singlet); 1.20 (1H, doublet, J=14.6 Hz); 1.86 (1H, doublet, J=14.6 Hz); 4.45 (1H, doublet, J=13.9 Hz); 4.82 (1H, singlet); 5.24 (1H, doublet, J=13.9 Hz); 7.11 (1H, doublet of doublets, J=2.5 and 8.4 Hz); 7.19 (1H, doublet, J=8.4 Hz); 7.69 (1H, doublet, J=2.5 Hz); 7.48 (1H, singlet); 7.87 (1H, singlet).
Mass spectrum (m/z): 343, 328, 261, 173.

Example 28

1-(1H-1,2,4-Triazol-1-yl)-2-(2,3,4-trichlorophenyl)-3-trimethylsilyl-2-propanol (Compound No. 1-64)

11.4 mg, yield 5%.
melting at 170°-172° C.
Nuclear Magnetic Resonance Spectrum (CDCl$_3$) δ ppm: −0.15 (9H, singlet); 1.24 (1H, doublet, J=14.7 Hz); 1.90 (1H, doublet of doublets, J=14.7 and 1.8 Hz); 4.45 (1H, doublet, J=14.1 Hz); 4.96 (1H, doublet, J=1.8 Hz); 5.28 (1H, doublet, J=14.1 Hz); 7.27 (1H, doublet, J=8.8 Hz); 7.59 (1H, doublet, J=8.8 Hz); 7.82 (1H, singlet); 7.86 (1H, singlet).
Mass spectrum (m/z): 378, 362, 295, 207.

Example 29

1-(1H-1,2,4-Triazol-1-yl)-2-(2,4,5-trichlorophenyl)-3-trimethylsilyl-2-propanol (Compound No. 1-65)

9.9 mg, yield 4.4%.
melting at 139°-141° C.
Nuclear Magnetic Resonance Spectrum (CDCl$_3$) δ ppm: −0.13 (9H, singlet); 1.21 (1H, doublet, J=14.7 Hz); 1.80 (1H, doublet, J=14.7 Hz); 4.42 (1H, doublet, J=14.0 Hz); 4.93 (1H, singlet); 5.18 (1H, doublet, J=14.0 Hz); 7.40 (1H, singlet); 7.80 (1H, singlet); 7.86 (1H, singlet); 7.89 (1H, singlet).
Mass spectrum (m/z): 378, 363, 297, 252.

Example 30

2-(3,4-Methylenedioxyphenyl)-1-(1H-1,2,4-triazol-1-yl)-trimethylsilyl-2-propanol (Compound No. 1-66)

49 mg, yield 22%.
melting at 156°-157° C.
Nuclear Magnetic Resonance Spectrum (CDCl$_3$) δ ppm: −0.118 (9H, singlet); 1.68 (1H, doublet, J=14.6 Hz); 1.89 (1H, doublet, J=14.6 Hz); 2.98-3.50 (1H, broad); 4.25 (1H, doublet, J=8.1 Hz); 4.15 (1H, doublet, J=7.1 Hz); 5.97 (2H, singlet); 6.58 (1H, doublet, J=2.2 Hz); 6.61 (1H, doublet of doublets, J=2.2 and 8.4 Hz); 6.78 (1H, doublet, J=8.4 Hz); 7.99 (1H, singlet); 8.18 (1H, singlet).
Mass spectrum (m/z): 319, 304, 288, 147.

Example 31

2-(4-Fluorophenyl)-1-(1H-1,2,4-triazol-1-yl)-3-trimethyl silyl-2-propanol oxalate (Compound No. 1-74)

9 mg (0.0001 mole) of oxalic acid were added at room temperature to 2 ml of a diethyl ether solution containing 59 mg (0.0002 mole) of 2-(4-fluorophenyl)-1-(1H-1,2,4-triazol-1-yl)-3-trimetylsilyl-2-propanol (prepared as described in Example 2). The crystals which separated were collected by filtration and washed with diethyl ether, to obtain 50 mg (yield 74%) of the title compound as crystals, melting at 162°-163° C.
Nuclear Magnetic Resonance Spectrum (tetradeuterated methanol) δ ppm: −0.199 (9H, singlet); 1.31 (1H, doublet, J=14.8 Hz); 1.56 (1H, doublet, J=14.8 Hz); 4.58 (1H, doublet, J=14.0 Hz); 4.71 (1H, doublet, J=14.0 Hz); 6.97-7.06 (2H, multiplet); 7.40-7.47 (2H, multiplet); 8.40 (1H, singlet); 9.04 (1H, singlet).

EXAMPLE 32

2-(4-Fluorophenyl)-1-(1H-1,2,4-triazol-1-yl)3-trimethylsilyl-2-propanol nitrate (Compound No. 1-75)

Following a procedure similar to that described in Example 31, but using an equivalent amount of nitric acid in place of the oxalic acid, 60 mg (yield 86%) of the title compound were obtained as crystals, melting at 158°-160° C.
Nuclear Magnetic Resonance Spectrum (tetradeuterated methanol) δ ppm: −0.21 (9H, singlet); 1.29 (1H, doublet, J=14.7 Hz); 1.49 (1H, doublet, J=14.7 Hz); 4.45 (1H, doublet, J=14.1 Hz); 4.55 (1H, doublet, J=14.1 Hz); 6.95-7.04 (2H, multiplet); 7.37-7.44 (2H, multiplet); 7.85 (1H, singlet); 8.17 (1H, singlet).

EXAMPLE 33

Adduct of 2-(4-fluorophenyl)-1-(1H1,2,4-triazol-1-yl)-3-trimethylsilyl-2-propanol with saccharin (Compound No. 1-78)

147 mg (0.0005 mole) of 2-(4 fluorophenyl)-1-(1H-1,2,4-triazol-1-yl)-3-trimethylsilyl-2-propanol (prepared as described in Example 2) and 92 mg (0.0005 mole) of saccharin were dissolved in 5 ml of methanol whilst stirring at room temperature The methanolic reaction solution was then condensed by evaporation under reduced pressure, to give 238 mg (yield 100%) of the title compound, as crystals, melting at 107°-108° C.
Nuclear Magnetic Resonance Spectrum (tetradeuterated methanol) δ ppm: −0.21 (9H, singlet); 1.24 (1H, doublet, J=14.6 Hz); 4.48 (1H, doublet, J=15.2 Hz); 4.54 (1H, doublet, J=15.2 Hz); 6.94-7.03 (2H, multiplet); 7.37-7.44 (2H, multiplet); 7.84 (1H, singlet); 7.87-8.03 (4H, multiplet). 8.16 (1H, singlet).

EXAMPLE 34

Adduct of 2-(4-chlorophenyl)-1-(1H-1,2,4-triazol-1-yl)-3-trimethylsilyl-2-propanol with saccharin (Compound No. 1-83)

Following a procedure similar to that described in Example 33, but using an equivalent amount of 2-(4-chlorophenyl)-1-(1H-1,2,4-triazol-1-yl)-3-trimethylsilyl-2-propanol (prepared as described in Example 3) in place of the 2-(4-fluorophenyl)-1-(1H-1,2,4-triazol-1-yl)-3-trimethylsilyl-2-propanol, 247 mg (yield 100%) of the title compound were obtained as crystals, melting at 208°-210° C.
Nuclear Magnetic Resonance Spectrum (tetradeuterated methanol) δ ppm: −0.202 (9H, singlet); 1.25 (1H, doublet, J=14.7 Hz); 1.48 (1H, doublet, J=14.7 Hz); 4.44 (1H, doublet, J=14.1 Hz); 4.55 (1H, doublet, J=14.1 Hz); 7.24-7.40 (4H, multiplet); 7.84 (1H, singlet); 7.84-8.05 (4H, multiplet); 8.17 (1H, singlet).

EXAMPLES 35 TO 38

The following compounds were synthesized in a similar manner to that described in Example 2.

Example 35

2-(4-Chlorophenyl)-3-dimethylphenylsilyl-1-(1H-1,2,4-triazol-1-yl)-2-propanol (Compound No. 1-67)

44.8 mg, yield 20%.
melting at 73°–82° C.
Nuclear Magnetic Resonance Spectrum (CDCl$_3$) δ ppm: 0.038 (3H, singlet); 0.16 (3H, singlet); 1.39 (1H, doublet, J=14.6 Hz); 1.56 (1H, doublet, J=14.6 Hz); 4.31 (1H, doublet, J=11.0 Hz); 4.33 (1H, doublet, J=11.0 Hz); 7.26–7.35 (9H, multiplet); 7.83 (2H, singlet)
Mass spectrum (m/z): 371, 356, 269, 211, 135.

Example 36

3-Dimethylphenylsilyl-2-(4-fluorophenyl)-1-(1H-1,2,4-triazol-1-yl)-2-propanol (Compound No. 1-68)

30.6 mg, yield 15%.
oily substance.
Nuclear Magnetic Resonance Spectrum (CDCl$_3$) δ ppm: 0.02 (3H, singlet); 0.15 (3H, singlet); 1.39 (1H, doublet, J=14.6 Hz); 1.57 (1H, doublet, J=14.6 Hz); 4.29 (1H, doublet, J=13.0 Hz); 4.30 (1H, doublet, J=13.0 Hz); 6.90 (2H, doublet of doublets, J=8.70 and 8.70 Hz); 7 17–7.35 (7H, multiplet); 7.73 (1H, singlet); 7.84 (1H, singlet).
Mass spectrum (m/z): 355, 340, 273, 196, 137.

Example 37

3-[(4-Chlorophenyl)dimethylsilyl]-2-(4-fluorophenyl)-1-(1H-1,2,4-triazol-1-yl)-2-propanol (Compound No. 1-69)

93 mg, yield 11%.
amorphous.
Nuclear Magnetic Resonance Spectrum (CDCl$_3$) δ ppm: 0.02 (3H, singlet); 0.16 (3H, singlet); 1.38 (1H, doublet, J=4.6 Hz); 1.53 (1H, doublet, J=4.6 Hz); 4.31 (2H, singlet); 6.90 (2H, doublet of doublets, J=8.7 and 8.7 Hz); 7.20 (2H, doublet of doublets, J=8.7 and 5.3 Hz); 7.25 (4H, singlet); 7.72 (1H, singlet); 7.87 (1H, singlet).
Mass spectrum (m/z): 389, 374, 307, 276, 195.

Example 38

3-Dimethylethylsilyl-2-(4-fluorophenyl)-1-(1H-1,2,4-triazol-1-yl)-2-propanol (Compound No. 1-70)

71 mg, yield 29%.
melting at 74°–76.5° C.
Nuclear Magnetic Resonance Spectrum (CDCl$_3$) δ ppm: −0.26 (3H, singlet); −0.19 (3H, singlet); 0.32 (1H, quartet, J=7.8 Hz); 0.30 (1H, quartet, J=7.8 Hz); 0.79 (3H, triplet, J=7.8 Hz); 1.14 (1H, doublet, J=4.6 Hz); 1.31 (1H, doublet, J=4.6 Hz); 4.20 (1H, singlet); 4.35 (2H, singlet); 7.30 (2H, doublet of doublets, J=8.8 and 5.1 Hz); 7.73 (1H, singlet); 7.88 (1H, singlet);
Mass spectrum (m/z): 292, 276, 225.

Example 39

2(4-Fluorophenyl)-1-(1H-1,2,4-triazol-1-yl)-3-trimethylsilyl-2-propanol (Compound No. 1-3)

0.237 g (6.18 mmole) of a 60% w/v dispersion of sodium hydride in mineral oil was added to 10 ml of dimethylacetamide. The mixture was then cooled in an ice-water bath, after which 0.854 g (12.37 mmole) of 1,2,4-triazole was added, whilst stirring. The reaction mixture was stirred for 30 minutes, and then 1.4 g (6.24 mmole) of 2-(4-fluorophenyl)-2-trimethylsilylmethyloxirane (prepared as described in Example 66) were added. The mixture was stirred for a further 2 hours at 80° C., after which it was cooled, and the mixture was poured into 50 ml of ice water and extracted with 100 ml of ethyl acetate. The organic extract was washed twice, each time with 50 ml of a saturated aqueous solution of sodium chloride, and then dried over anhydrous sodium sulfate. The solvent was then removed by distillation under reduced pressure, to obtain crude crystals These crystals were recrystallized from diisopropyl ether, to give 1.01 g (yield 55%) of the title compound, as crystals, melting at 118°–119° C.

Example 40

1-Chloro-2-(4-fluorophenyl)-3-trimethylsilyl-2-propanol (Compound No. 2-3)

8.63 g (0.05 mole) of 2-chloro-4'-fluoroacetophenone were dissolved in 60 ml of diethyl ether. The solution was stirred under a stream of nitrogen, and 200 ml (0.057 mole) of a diethyl ether solution of trimethylsilylmethylmagnesium chloride were added dropwise at such a rate that the temperature of the reaction mixture did not rise above 15° C.–20° C. The reaction mixture was then stirred for a further 1 hour at room temperature, after which it was poured into 200 ml of ice water, and its pH was adjusted to a value of 6–7 by the addition of 5% w/v aqueous hydrochloric acid. It was then extracted with 100 ml of ethyl acetate. The organic extract was washed twice, each time with 50 ml of a saturated aqueous solution of sodium chloride It was then dried over anhydrous sodium sulfate, and the solvent was removed by distillation under reduced pressure, to afford a crude oily product. This crude oily product was purified by silica gel column chromatography, using mixtures of ethyl acetate and hexane ranging from 1:10 to 1:5 by volume, to give 8.8 g (yield 67.7%) of the title compound as an oily substance.

Elemental analysis Calculated for $C_{12}H_{18}ClFOSi$: C, 55.26%; H, 6.96%; Cl, 13.59%; F, 7.26%. Found: C, 55.02%; H, 6.96%; C:, 13.58%; F, 7.43%.

Nuclear Magnetic Resonance Spectrum (CDCl$_3$) δ ppm: −0.18 (9H, singlet); 1.23 (1H, doublet, J=14.7 Hz); 1.45 (1H, doublet, J=14.7 Hz); 3.70 (1H, doublet, J=11.0 Hz); 3.80 (1H, doublet, J=11.0 Hz); 6.99–7.09 (2H, multiplet); 7.35–7.43 (2H, multiplet).

EXAMPLES 41 TO 65

A procedure similar to that described in Example 40 was repeated, to give the following compounds.

Example 41

1-Chloro-2-(4-chlorophenyl)-3-trimethylsilyl-2-propanol (Compound No. 2-2)

1.287 g, yield 93%.
oily substance.
Nuclear Magnetic Resonance Spectrum (CDCl$_3$) δ ppm: −0.17 (9H, singlet); 1.44 (1H, doublet, J=14.7 Hz); 1.23 (1H, doublet, J=14.7 Hz); 2.59 (1H, singlet); 3.74 (1H, doublet, J=11.0 Hz); 3.80 (1H, doublet, J=11.0 Hz); 7.29–7.39 (4H, multiplet).

Example 42

1-Chloro-2-(2,4-difluorophenyl)-3-trimethylsilyl-2-propanol (Compound No. 2-12)

323 mg, yield 58%.
oily substance.
Nuclear Magnetic Resonance Spectrum (CDCl$_3$) δ ppm: −0.17 (9H, singlet); 1.30 (1H, doublet, J=15.3 Hz); 1.49 (1H, doublet, J=15.3 Hz); 2.72 (1H, singlet); 3.82 (1H, doublet, J=10.8 Hz); 4.07 (1H, doublet, J=10.8 Hz); 6.73–6.96 (2H, multiplet); 7.56–7.65 (1H, multiplet).

Example 43

1-Chloro-2-(4-chloro-2-fluorophenyl)-3-trimethylsilyl-2-propanol (Compound No. 2-14)

1.08 g, yield 98%.
oily substance.
Nuclear Magnetic Resonance Spectrum (CDCl$_3$) δ ppm: −0.17 (9H, singlet); 1.30 (1H, doublet, J=14.7 Hz); 1.49 (1H, doublet, J=14.7 Hz); 2.72 (1H, singlet); 3.81 (1H, doublet, J=11.0 Hz); 4.07 (1H, doublet, J=11.0 Hz); 7.03 (2H, multiplet); 7.58 (1H, multiplet).

Example 44

1-Chloro-2-phenyl-3-trimethylsilyl-2-propanol (Compound No. 2-1)

1.02 g, yield 84%.
oily substance.
Nuclear Magnetic Resonance Spectrum (CDCl$_3$) δ ppm: −0.19 (9H, singlet); 1.26 (1H, doublet, J=14.6 Hz); 1.46 (1H, doublet, J=14.6 Hz); 2.60 (1H, singlet); 3.78 (1H, doublet, J=10.8 Hz); 3.86 (1H, doublet, J=10.8 Hz); 7.27–7.45 (5H, multiplet).

Example 45

1-Chloro-2-(2,4-dichlorophenyl)-3-trimethylsilyl-2-propanol (Compound No. 2-11)

928 mg, yield 60%.
oily substance.
Nuclear Magnetic Resonance Spectrum (CDCl$_3$) δ ppm: −0.17 (9H, singlet); 1.29 (1H, doublet, J=14.4 Hz); 1.90 (1H, doublet of doublets, J=14.4 and 1.4 Hz); 2.81 (1H, doublet, J=1.4 Hz); 3.90 (1H, doublet, J=11.0 Hz); 4.48 (1H, doublet, J=11.0 Hz); 7.30 (1H, doublet of doublets, J=8.6 and 2.2 Hz); 7.38 (1H, doublet, J=2.2 Hz); 7.78 (1H, doublet, J=8.6 Hz).

Example 46

1-Bromo-2-(4-methoxyphenyl)-3-trimethylsilyl-2-propanol (Compound No. 2-45)

195 mg, yield 13%.
oily substance.
Nuclear Magnetic Resonance Spectrum (CDCl$_3$) δ ppm: −0.19 (9H, singlet); 1.29 (1H, doublet, J=15.5 Hz); 1.49 (1H, doublet, J=15.5 Hz); 2.49 (1H, singlet); 3.71 (1H, doublet, J=10.0 Hz); 3.75 (1H, doublet, J=10.0 Hz); 3.81 (3H, singlet); 6.82–6.97 (2H, multiplet); 7.21–7.47 (2H, multiplet).

Example 47

1-Bromo-2-(3-methoxyphenyl)-3-trimethylsilyl-2-propanol (Compound No. 2-21)

872 mg, yield 58%.
oily substance
Nuclear Magnetic Resonance Spectrum (CDCl$_3$) δ ppm: −0.18 (9H, singlet); 1.30 (1H, doublet, J=14.6 Hz); 1.47 (1H, doublet, J=14.6 Hz); 2.46–2.63 (1H, broad); 3.73 (1H, doublet, J=10.2 Hz); 3.83 (1H, doublet, J=10.2 Hz); 6.78–6.84 (1H, multiplet); 6.97–7.02 (2H, multiplet); 7.23–7.31 (1H, multiplet).

Example 48

1-Bromo-2-(2-methoxyphenyl)-3-trimethylsilyl-2-propanol (Compound No. 2-53)

546 mg, yield 36%.
oily substance.
Nuclear Magnetic Resonance Spectrum (CDCl$_3$) δ ppm: −0.21 (9H, singlet); 1.77 (1H, doublet of doublets, J=14.7 and 1.7 Hz); 7.09 (1H, doublet, J=14.7 Hz); 3.05 (1H, doublet, J=1.7 Hz); 3.83 (1H, doublet, J=9.7 Hz); 4.23 (1H, doublet, J=9.7 Hz); 6.86–7.02 (2H, multiplet); 7.24–7.29 (1H, multiplet); 7.52–7.57 (1H, multiplet).

Example 49

1-Bromo-2-(4-ethylphenyl)-3-trimethylsilyl-2-propanol (Compound No. 2-48)

401 mg, yield 25%.
oily substance.
Nuclear Magnetic Resonance Spectrum (CDCl$_3$) δ ppm: −0.20 (9H, singlet); 1.23 (3H, triplet, J=7.6 Hz); 1.30 (1H, doublet, J=14.6 Hz); 1.48 (1H, doublet, J=14.6 Hz); 2.52 (1H, singlet); 2.65 (2H, quartet, J=7.6 Hz); 3.74 (1H, doublet, J=10.1 Hz); 3.80 (1H, doublet, J=10.1 Hz); 7.15–7.35 (4H, multiplet).

Example 50

1-Bromo-2-(4-phenylphenyl)-3-trimethylsilyl-2-propanol (Compound No. 2-46)

472 mg, yield 26%.
oily substance
Nuclear Magnetic Resonance Spectrum (CDCl$_3$) δ ppm: −0.16 (9H, singlet); 1.35 (1H, doublet, J=14.6 Hz); 1.53 (1H, doublet, J=14.6 Hz); 2.59 (1H, singlet); 3.78 (1H, doublet, J=10.1 Hz); 3.84 (1H, doublet, J=10.1 Hz); 7.31–7.50 (5H, multiplet); 7.57–7.65 (4H, multiplet).

Example 51

1-Bromo-2-(2-chloro-4-fluorophenyl)-3-trimethylsilyl-2-propanol (Compound No. 2-13)

841 mg, yield 83%.
oily substance.
Nuclear Magnetic Resonance Spectrum (CDCl$_3$) δ ppm: −0.18 (9H, singlet); 1.29 (1H, doublet, J=14.8 Hz); 1.91 (1H, doublet, J=14.8 Hz); 2.72–2.90 (1H, broad); 3.92 (1H, doublet, J=11.0 Hz); 4.46 (1H, doublet, J=11.0 Hz); 6.98–7.14 (2H, multiplet); 7.78–7.86 (1H, multiplet).

Example 52

1-Bromo-2-(2-chlorophenyl)-3-trimethylsilyl-2-propanol (Compound No. 2-54)

175 mg, yield 11%.
oily substance
Nuclear Magnetic Resonance Spectrum (CDCl$_3$), δ ppm: −0.19 (9H, singlet); 1.33 (1H, doublet, J=14.7 Hz); 2.03 (1H, doublet of doublets, J=14.7 and 1.8 Hz); 2.76 (1H, doublet, J=1.8 Hz); 3.89 (1H, doublet, J=10.2 Hz); 4.52 (1H, doublet, J=10.2 Hz); 7.22–7.38 (3H, multiplet); 7.78–7.83 (1H, multiplet).

Example 53

1-Bromo-2-(3-bromophenyl)-3-trimethylsilyl-2-propanol (Compound No. 2-61)

733 mg, yield 36%
oily substance.
Nuclear Magnetic Resonance Spectrum (CDCl$_3$) δ ppm: −0.17 (9H, singlet); 1.28 (1H, doublet, J=14.7 Hz); 1.47 (1H, doublet, J=14.7 Hz); 2.56 (1H, singlet); 3.71 (1H, doublet, J=10.3 Hz); 3.76 (1H, doublet, J=10.3 Hz); 7.19–7.44 (3H, multiplet); 7.58–7.59 (1H, multiplet).

Example 54

1-Bromo-2-(3-methylphenyl)-3-trimethylsilyl-2-propanol (Compound No. 2-62)

471 mg, yield 31%.
oily substance.
Nuclear Magnetic Resonance Spectrum (CDCl$_3$) δ ppm: −0.19 (9H, singlet); 1.31 (1H, doublet, J=15.1 Hz); 1.42 (1H, doublet, J=15.1 Hz); 2.37 (3H, singlet); 2.52 (1H, singlet); 3.74 (1H, doublet, J=10.2 Hz); 3.80 (1H, doublet, J=10.2 Hz); 7.06–7.28 (4H, multiplet).

Example 55

1-Bromo-2-(2-fluorophenyl)-3-trimethylsilyl-2-propanol (Compound No. 2-74)

272 mg, yield 18%.
oily substance
Nuclear Magnetic Resonance Spectrum (CDCl$_3$) δ ppm: −0.20 (9H, singlet); 1.34 (1H, doublet, J=14.7 Hz); 1.60 (1H, doublet of doublets, J=14.7 and 1.6 Hz); 2.68 (1H, doublet, J=1.6 Hz); 3.81 (1H, doublet, J=10.1 Hz); 4.10 (1H, doublet, J=10.1 Hz); 6.96–7.00 (1H, multiplet); 7.18–7.31 (2H, multiplet); 7.57–7.66 (1H, multiplet).

Example 56

1-Bromo-2-(2,5-dichlorophenyl)-3-trimethylsilyl-2-propanol (Compound No. 2-63)

275 gm, yield 15%.
oily substance.
Nuclear Magnetic Resonance Spectrum (CDCl$_3$) δ ppm: −0.16 (9H, singlet); 1.33 (1H, doublet, J=14.8 Hz); 1.96 (1H, doublet of doublets, J=14.8 and 1.6 Hz); 2.77 (1H, doublet, J=1.6 Hz); 3.84 (1H, doublet, J=10.3 Hz); 4.49 (1H, doublet, J=10.3 Hz); 7.18–7.31 (2H, multiplet); 7.82 (1H, doublet, J=2.49 Hz).
Mass spectrum (m/z): 356, 261, 187, 171.

Example 57

1-Bromo-2-(2,3,4-trichlorophenyl)-3-trimethylsilyl-2-propanol (Compound No. 2-64)

212 mg, yield 12%.
oily substance.
Nuclear Magnetic Resonance Spectrum (CDCl$_3$) δ ppm: −0.16 (9H, singlet); 1.34 (1H, doublet, J=14.8 Hz); 1.99 (1H, doublet of doublets, J=14.8 and 1.0 Hz); 2.81 (1H, doublet, J=1.0 Hz); 3.84 (1H, doublet, J=10.4 Hz); 4.55 (1H, doublet, J=10.4 Hz); 7.43 (1H, doublet, J=8.8 Hz); 7.57 (1H, doublet, J=8.8 Hz).

Example 58

1-Chloro-2-(2,4,5-trichlorohenyl)-3-trimethylsilyl-2-propanol (Compound No. 2-65)

199 mg, yield 45%.
oily substance.
Nuclear Magnetic Resonance Spectrum (CDCl$_3$) δ ppm: −0.13 (9H, singlet); 1.30 (1H, doublet, J=14.8 Hz); 1.84 (1H, doublet of doublets, J=14.8 and 1.5 Hz); 2.84 (1H, doublet, J=1.5 Hz); 3.87 (1H, doublet, J=11 1 Hz); 4.48 (1H, doublet, J=Il.1 Hz); 7.47 (1H, singlet); 7.93 (1H, singlet).

Example 59

1-Bromo-2-(3,4-methylenedioxyphenyl)-3-trimethylsilyl-2-propanol (Compound No. 2-66)

337 mg, yield 11%
oily substance.
Nuclear Magnetic Resonance Spectrum (CDCl$_3$) δ ppm: −0.16 (9H, singlet); 1.26 (1H, doublet, J=14.6 Hz); 1.46 (1H, doublet, J=14.6 Hz); 2.49 (1H, singlet); 3.69 (1H., doublet, J=10.6 Hz); 3.74 (1H, doublet, J=10.6 Hz); 5.97 (2H, singlet); 6.00–6.92 (3H, multiplet).
Mass spectrum (m/z): 330, 237, 221, 147.

Example 60

1-Bromo-2-(4-methylphenyl)-3-trimethylsilyl-2-propanol (Compound No. 2-73)

272 mg, yield 18%.
oily substance.
Nuclear Magnetic Resonance Spectrum (CDCl$_3$) δ ppm: −0.19 (9H, singlet); 1.30 (1H, doublet of doublets, J=14.5 and 1.0 Hz); 1.48 (1H, doublet, J=14.5 Hz); 2.35 (3H, singlet); 2.51 (1H, doublet, J=1.0 Hz); 2.73 (1H, doublet, J=10.1 Hz); 2.88 (1H, doublet, J=10.1 Hz); 7.15 (2H, doublet, J=8.3 Hz); 7.28 (2H, doublet, J=8.3 Hz).

Example 61

1-Chloro-2-(4-fluorophenyl)-3-dimethylethylsilyl-2-propanol (Compound No. 2-70)

720 mg, yield 87%.
oily substance.
Nuclear magnetic Resonance Spectrum (CDCl$_3$), δ ppm: −0.25 (3H, singlet); −0.18 (3H, singlet); 0.31 (2H, quartet, J=7.6 Hz); 0.81 (3H, triplet, J=7.6 Hz); 1.23 (1H, doublet, J=14.7 Hz); 1.45 (1H, doublet, J=14.7 Hz); 2.59 (1H, singlet); 3.81 (1H, doublet, J=10 9 Hz); 3.75 (1H, doublet, J=10.9 Hz); 7.04 (2H, doublet of doublets, J=8.8 and 8.8 Hz); 7.40 (2H, doublet of doublets, J=8.8 and 5.3 Hz).
Mass spectrum (m/z): 256 (M$^+$−18), 245, 225, 170, 135.

Example 62

1-Chloro-3-[(4-chlorophenyl)dimethylsilyl]-2-(4-fluorophenyl)-2-propanol (Compound No. 2-69)

985 mg, yield 69%.
oily substance.
Nuclear Magnetic Resonance Spectrum (CDCl$_3$) δ ppm: 0.01 (3H, singlet); 0.17 (3H, singlet); 1.45 (1H, doublet, J=4.8 Hz); 1.70 (1H, doublet, J=4.8 Hz); 2.56 (1H, singlet); 3.72 (2H, singlet); 6.97 (2H, doublet of doublets, J=8.8 and 8.8 Hz); 7.27 (4H, singlet); 7.30 (2H, doublet of doublets, J=8.8 and 5.2 Hz).

Mass spectrum (m/z): 356 (M+), 341, 307, 195.

Example 63

1-Chloro-2-(3,4-dichlorophenyl)-3-trimethylsilyl-2-propanol (Compound No. 2-29)

614 mg, yield 66%.

oily substance.

Nuclear Magnetic Resonance Spectrum (CDCl₃), δ ppm: −0.14 (9H, singlet); 1.21 (1H, doublet, J=14.7 Hz); 1.43 (1H, doublet, J=14.7 Hz); 2.67 (1H, singlet); 3.72 (1H, doublet, J=11.1 Hz); 3.79 (1H, doublet, J=11.1 Hz); 7.23 (1H, doublet of doublets, J=8.4 and 2.2 Hz); 7.43 (1H, doublet, J=8.4 Hz); 7.54 (1H, doublet, J=2.2 Hz).

Example 64

1-Chloro-2-(4-chlorophenyl)-3-dimethylphenyl-2-propanol (Compound No. 2-67)

720 mg, yield 30%.

oily substance.

Nuclear Magnetic Resonance Spectrum (CDCl₃) δ ppm: −0.03 (3H, singlet); 0.19 (3H, singlet); 1.47 (1H, doublet, J=14.8 Hz); 1.71 (1H, doublet, J=14.8 Hz); 3.71 (2H, singlet); 7.26–7.38 (9H, multiplet).

Mass spectrum (m/z): 340 (M+ +1), 304, 211, 141, 111.

Example 65

1-Chloro-3-dimethylphenylsilyl-2-(4-fluorophenyl)-2-propanol (Compound No. 2-68)

517 mg, yield 22%.

oily substance.

Nuclear Magnetic Resonance Spectrum (CDCl₃) δ ppm: 0.014 (3H, singlet); 0.18 (3H, singlet); 1.48 (1H, doublet, J=14.8 Hz); 1.72 (1H, doublet, J=14.8 Hz); 3.72 (2H, singlet); 6.98 (2H, triplet, J=8.8 Hz); 7.26–7.41 (7H, multiplet).

Mass spectrum (m/z): 407, 354, 322, 273, 195, 170.

Example 66

2-(4-Fluorophenyl)-2-trimethylsilylmethyloxirane (Compound No. 3.3)

1.068 g (6.2 mmole) of 2-chloro-4'-fluoroacetophenone were dissolved in 20 ml of diethyl ether, and the ethereal solution was stirred under a stream of nitrogen, whilst 7.5 ml of an ethereal solution containing 7.4 mmole of trimethylsilylmethylmagnesium chloride was added dropwise at such a rate that the temperature of the reaction mixture did not exceed −10° C. to −5° C. The reaction mixture was then stirred for a further 15 minutes whilst being kept within this temperature range. At the end of this time, 3.5 ml of dimethylformamide were added dropwise to the reaction solution at such a rate that the temperature of the reaction mixture did not exceed −10° C. to −5° C. The reaction mixture was then stirred for a further 10 minutes and, whilst it was being kept within this temperature range, 6 ml of hexane and then 6 ml of water were added. The reaction mixture was then stirred for 5 minutes, after which it was poured into 10 ml of water and extracted with 100 ml of hexane. The organic extract was washed with 50 ml of a saturated aqueous solution of sodium chloride and dried over anhydrous sodium sulfate. The solvent was then removed by distillation under reduced pressure, to give 1.39 g (yield 100%) of the title compound, as an oily substance.

Nuclear Magnetic Resonance Spectrum (CDCl₃), δ ppm: −0.082 (9H, singlet); 1.31 (1H, doublet, J=14.7 Hz); 1.44 (1H, doublet, J=14.7 Hz); 2.78 (1H, doublet, J=5.3 Hz); 2.90 (1H, doublet, J=5.3 Hz); 6.96–7.05 (2H, multiplet); 7.32–7.39 (2H, multiplet).

Mass spectrum (m/z): 224, 209, 195, 135.

EXAMPLES 67 TO 73

The following compounds were synthesized in a similar manner to that described in Example 66.

Example 67

2-Phenyl-2-trimethylsilylmethyloxirane (Compound No. 3-1)

39 mg, yield 75%. oily substance.

Nuclear Magnetic Resonance Spectrum (CDCl₃) δ ppm: −0.084 (9H, singlet); 1.37 (1H, doublet, J=14.6 Hz); 1.47 (1H, doublet, J=14.6 Hz); 2.82 (1H, doublet, J=5.1 Hz); 2.91 (1H, doublet, J=5.1 Hz); 7.25–7.42 (5H, multiplet).

Mass spectrum (m/z): 206, 191, 117.

Example 68

2-(4-Chlorophenyl)-2-trimethylsilylmethyloxirane (Compound No. 3-2)

47 mg, yield 78%.

oily substance.

Nuclear Magnetic Resonance Spectrum (CDCl₃), δ ppm: −0.071 (9H, singlet); 1.28 (1H, doublet, J=14.7 Hz); 1.47 (1H, doublet, J=14.7 Hz); 2.74 (1H, doublet, J=5.3 Hz); 2.90 (1H, doublet, J=5.3 Hz); 7.26–7.46 (4H, multiplet).

Mass spectrum (m/z): 240, 227, 211, 151, 137.

Example 69

2-(4-Methylphenyl)-2-trimethylsilylmethyloxirane (Compound No. 3-31)

45 mg, yield 82%.

oily substance

Nuclear Magnetic Resonance Spectrum (CDCl₃) δ ppm: −0.084 (9H, singlet); 1.34 (1H, doublet, J=14.0 Hz); 1.43 (1H, doublet, J=14.0 Hz); 2.33 (3H, singlet); 2.28 (1H, doublet, J=5.4 Hz); 2.89 (1H, doublet, J=5.4 Hz); 7.10–7.34 (4H, multiplet).

Mass spectrum (m/z): 220, 205, 191, 148, 130.

Example 70

2-(2,4-Difluorophenyl)-2-trimethylsilylmethyloxirane (Compound No. 3-8)

29 mg, yield 48%.

oily substance.

Nuclear Magnetic Resonance Spectrum (CDCl₃) δ ppm: −0.089 (9H, singlet); 1.32 (1H, doublet, J=14.6 Hz); 1.39 (1H, doublet, J=14.6 Hz); 2.83 (1H, doublet, J=5.2 Hz); 2.90 (1H, doublet, J=5.2 Hz); 6.72–6.89 (2H, multiplet); 7.31–7.44 (1H, multiplet).

Mass spectrum (m/z): 241, 227, 207, 153.

Example 71

2-(4-Chloro-2-fluorophenyl)-2-trimethylsilylmethyloxirane (Compound No. 3-10)

41 mg, yield 63%.

oily substance.

Nuclear Magnetic Resonance Spectrum (CDCl₃) δ ppm: −0.084 (9H, singlet); 1.30 (1H, doublet, J=14.8 Hz); 1.41 (1H, doublet, J=14.8 Hz); 2.81 (1H, doublet, J=5.2 Hz); 2.90 (1H, doublet, J=5.2 Hz); 7.03-7.13 (2H, multiplet); 7.27-7.38 (1H, multiplet).

Mass spectrum (m/z): 257, 243, 223, 208, 169.

Example 72

2-(2,4-Dichlorophenyl)-2-trimethylsilylmethyloxirane (Compound No. 3-7)

65 mg, yield 94%.

oily substance.

Nuclear Magnetic Resonance Spectrum (CDCl3) δ ppm: −0.045 (9H, singlet); 1.32 (1H, doublet, J=14.9 Hz); 1.52 (1H, doublet, J=14.9 Hz); 2.76 (1H, doublet, J=5.1 Hz); 2.94 (1H, doublet, J=5.1 Hz); 7.19-7.41 (3H, multiplet).

Mass spectrum (m/z): 273, 259, 239, 185, 171.

Example 73

2-(2-Chlorophenyl)-2-trimethylsilylmethyloxirane (Compound No. 3-11)

376 mg, yield 80%.

oily substance.

Nuclear Magnetic Resonance Spectrum (CDCl) δ ppm: 0.062 (9H, singlet); 1.36 (1H, doublet, J=14.9 Hz); 1.54 (1H, doublet, J=14.9 Hz); 2.81 (1H, doublet, J=5.2 Hz); 2.95 (1H, doublet, J=5.2 Hz); 7.20-7.25 (2H, multiplet); 7.31-7.36 (1H, multiplet); 7.43-7.48 (1H, multiplet).

Mass spectrum (m/z): 240, 225, 211, 168.

FORMULATION EXAMPLES are by weight. The Compound Nos. used refer to those numbers assigned to the compounds in the foregoing Table 1. All mesh sizes use the Tyler standard.

FORMULATION EXAMPLE 1

Wettable Powder

A mixture containing 80% of Compound No. 3, 2% of sodium alkylnaphthalenesulfonate, 2% of sodium ligninsulfonate, 3% of hydrated silica and 13% of kaolinite was pulverized using a hammer mill. It was then mixed again and packaged.

FORMULATION EXAMPLE 2

Wettable Powder

A mixture containing 25% of Compound No. 2, 2.5% of sodium dodecylbenzenesulfonate, 2.5% of sodium ligninsulfonate, 55% of diatomaceous earth and 15% of hydrated silica was pulverized, to prepare a wettable powder.

FORMULATION EXAMPLE 3

Emulsifiable Concentrate

15% of Compound No. 3, 35% of cyclohexanone, 11% of polyoxyethylenenonyl phenyl ether, 4% of calcium dodecylbenzenesulfoante and 35% of methylnaphthalene were dissolved homogeneously, to prepare an emulsifiable concentrate.

FORMULATION EXAMPLE 4

Emulsifiable Concentrate

15% of Compound No. 12, 25% of calcium dodecylbenzenesulfoante blended with a non-ionic surfactant and 60% of xylene were mixed and stirred to dissolve the active ingredient.

FORMULATION EXAMPLE 5

Granule

5% of Compound No. 3, 2% of sodium laurylsulfate, 5% of sodium ligninsulfonate, 2% of sodium carboxymethyl. cellulose and 86% of clay were mixed until homogeneous and were then pulverized. One hundred parts by weight of the mixture were mixed with 20 parts by weight of water, and the mixture was kneaded into a paste. Using an extruding granulator, this mixture was processed into 14- to 32-mesh granules, and dried to prepare a granule formulation.

FORMULATION EXAMPLE 6

Granule

5% of Compound No. 2, 30% of bentonite, 62% of talc, 2% of sodium ligninesulfonate and 1% of sodium dodecylbenzenesulfonate were mixed until homogeneous and then pulverized. One hundred parts by weight of the mixture were then mixed with 20 parts by weight of water, and the mixture was kneaded into a paste. Using an extruding granulator, this mixture was processed into 14- to 32.mesh granules, and dried to prepare a granule formulation.

FORMULATION EXAMPLE 7

Granule

4% of Compound No. 12, 30% of bentonite, 63% of clay, 1% of polyvinyl alcohol and 2% of sodium dodecylbenzenesulfonate were mixed until homogeneous and the mixture was then pulverized. One hundred parts by weight of the resulting mixture were mixed with 20 parts by weight of water, and the mixture was kneaded into a paste. Using an extruding granulator, this mixture was processed into 14- to 32.mesh granules, and dried to prepare a granule formulation.

FORMULATION EXAMPLE 8

Granule

4% of Compound No. 3, 35% of bentonite, 58.8% of talc, 2% of sodium alkylnaphthalenesulfonate and 0.2% of sodium dioctylsulfosuccinate were mixed until homogeneous and the mixture was then pulverized. One hundred parts by weight of the mixture were mixed with 20 parts by weight of water, and the resulting mixture was kneaded into a paste. Using an extruding granulator, this mixture was processed into 14. to 32.mesh granules, and dried to prepare a granule formulation.

FORMULATION EXAMPLE 9

Granule

5% of Compound No. 12, 1% of white carbon, 5% of sodium ligninesulfonate, 84% of clay and 5% of sodium carboxymethylcellulose were thoroughly pulverized and mixed. Water was added, and the mixture was thoroughly kneaded. It was then processed into granules and dried to prepare a granule formulation.

FORMULATION EXAMPLE 10

Dust

2% of Compound No. 3, 5% of diatomaceous earth and 93% of clay were mixed until homogeneous. The mixture was then pulverized, to prepare the powder formulation.

FORMULATION EXAMPLE 11

Liquid formulation

10% of Compound No. 2 and 2% of sodium dodecyl benzenesulfonate were dissolved in 88% of water to prepare a liquid formulation.

FORMULATION EXAMPLE 12

Liquid Formulation

30% of Compound No. 3 and 70% of dimethyl sulfoxide were mixed and stirred to prepare a liquid formulation.

FORMULATION EXAMPLE 13

Granule 30 parts by weight of bentonite, 64.5 parts by weight of talc and 0.5 parts by weight of sodium dioctylsulfosuccinate were mixed until homogeneous. 18 parts by weight of water were added to 95 parts of the mixture, and the mixture was kneaded. The resulting paste was processed into granules using a granulator, and these were dried and passed through a sieve to obtain a granular carrier of size 14. to 32.mesh. 5% of Compound No. 12 was absorbed on 95% of the granular carrier, and mixed until homogeneous to prepare a granule formulation.

FORMULATION EXAMPLE 14

Granule

86% of clay, 0.5% of sodium dioctylsulfosuccinate, 7% of dextrin and 1.5% of sodium carboxymethylcellulose were mixed until homogeneous. 14 parts of water were added to 95 parts of the mixture, and the mixture was kneaded. The resulting paste was processed into granules using a granulator. These were dried and passed through a sieve to obtain a granular carrier of size 14 to 32.mesh. 5% of Compound No. 2 were absorbed on 95% of the granular carrier, and mixed until homogeneous to prepare a granule formulation.

FORMULATION EXAMPLE 15

Flowable Formulation 1 parts by weight of sodium dodecylbenzenesulfonate and 5 parts by weight of a polycondensate of sodium naphthalenesulfonate were dissolved in 41.8 parts by weight of water. 30 parts by weight of Compound No. 3 were suspended in this solution. The resulting suspension was pulverized using a sand mill to process it into granules having a mean diameter of 1.5 μm. Meanwhile, 0.2 parts by weight of xanthan gum and 2 parts by weight of magnesium aluminosilicate were dissolved and dispersed in 20 parts by weight of water, and the resulting dispersion was added to the ground slurry obtained as described above. The mixture was stirred until homogeneous, to obtain a suspension-type flowable formulation.

FORMULATION EXAMPLE 16

Flowable Formulation 5 parts by weight of Compound No. 3, 3.5 parts by weight of polyoxyethylenenonyl phenyl ether and 1.5 parts by weight of calcium dodecylbenzenesulfonate were mixed and dissolved until homogeneous. 56.65 parts by weight of water were then added, whilst stirring to emulsify the mixture, which was then processed using a homogenizer into a fine emulsion. Meanwhile, 0.35 parts by weight of xanthan gum and 3 parts by weight of magnesium aluminosilicate were dissolved and dispersed in 30 parts by weight of water, and the resulting solution was added to the emulsion obtained as described above. The mixture was then stirred until homogeneous to obtain an emulsion-type flowable formulation.

FORMULATION EXAMPLE 17

Granular Wettable Powder

60% of Compound No. 2, 15% of sodium lignin sulfonate, 17% of clay, 5% of granular calcium carbonate and 3% of sodium dodecylbenzenesulfonate were mixed and pulverized using a jet mill. The powder was then subjected to a fluidized bed granulator and drier in which water was sprayed onto it, to process it into granules. It was then dried and passed through a sieve to obtain 32. to 100.mesh granules as a granular wettable powder formulation.

We claim:

1. A compound of formula (I):

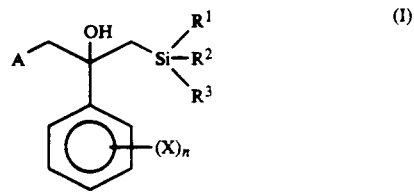

wherein:

A represents a 1,2,4-triazol-1-yl group;

n represents 0, 1, 2 or 3, and, when n represents 2 or 3, the groups represented by X may be the same or different;

X represents a halogen atom, a phenyl group, an alkyl group having from 1 to 6 carbon atoms, a haloalkyl group having from 1 to 6 carbon atoms and having at least one halogen atom, an alkoxy group having from 1 to 6 carbon atoms, or a haloalkoxy group having from 1 to 6 carbon atoms and having at least one halogen atom, or $(X)_n$ represents an alkylenedioxy group having 1 or 2 carbon atoms;

$R^1$ represents an alkyl group having from 1 to 4 carbon atoms or a phenyl group which is unsubstituted or is substituted by at least one halogen atom; and $R^2$ and $R^3$ are independently selected from the group consisting of alkyl groups having from 1 to 4 carbon atoms;

or a salt thereof.

2. The compound of claim 1, wherein n is 0, 1 or 2.

3. The compound of claim 1, wherein n is b 3 and X is at the 2,4 and 6 positions on the benzene ring.

4. The compound of claim 1, wherein n is 2 and X is at the 2 and 4 positions on the benzene ring.

5. The compound of claim 1, wherein n is 1 and X is at the 2 or the 4 position on the benzene ring.

6. The compound of claim 1, wherein:

n is 1 or 2, and X represents a fluorine atom, a chlorine atom, a bromine atom, an unsubstituted alkyl group having from 1 to 4 carbon atoms, a substituted alkyl group which has from 1 to 4 carbon atoms and which is substituted by from 1 to 3 halogen atoms, an unsubstituted alkoxy group having from 1 to 4 carbon atoms, or a substituted alkoxy group which has from 1 to 4 carbon atoms and which is substituted by from 1 to 3 halogen atoms; or n is 0; and R¹, R² and R³ are independently selected from the group consisting of alkyl gruops having 1 to 4 carbon atoms.

7. The compound of claim 1, wherein:

n is 1 or 2, and X represents a fluorine atom, a chlorine atom, a bromine atom, a trifluoromethyl group or a methoxy group, the substituent represented by X is at the 2-position and/or the 4-position of the benzene ring; or p1 n is 0; and R¹, R² and R³ are independently selected from the group consisting of methyl groups and ethyl groups.

8. The compound of claim 1, wherein:

n is 1 or 2, and X represents a fluorine atom, a chlorine atom or a bromine atom, and the substituent represented by X is at the 2-position and/or the 4-position of the benzene ring; or n is 0; and R¹, R² and R³ are independently selected from the group consisting of methyl gruops and ethyl groups.

9. The compound of claim 1, wherein:

n is 1 or 2, and X represents a fluorine atom, or a chlorine atom, and the substituent represented by X is at the 2-position and/or the 4-position of the benzene ring; or n is 0; and R¹, R² and R³ are all methyl groups.

10. The compound of claim 1, selected from the group consisting of 2-(4-chlorophenyl)-1-(1H-1,2,4-triazol-1-yl)-3-trimethylsilyl-2-propanol and salts thereof.

11. The compound of claim 1, selected from the group consisting of 2-(4-fluorophenyl)-1-(1H-1,2,4-triazol-1-yl)-3-trimethylsilyl-2-propanol and salts thereof.

12. The compound of claim 1, selected from the group consisting of 2-(2,4-difluorophenyl)-1-(1H-1,2,4-triazol-1-yl)-3-trimethylsilyl-2-propanol and salts thereof.

13. A pharmaceutical composition for the prevention or treatment of fungal infections, which comprises a fungicidally or fungistatically effective amount of an anti-fungal agent, wherein the anti-fungal agent is selected from the group consisting of compounds of formula (I) and pharmaceutically acceptable salts thereof, as claimed in claim 1.

14. The composition of claim 13, wherein:

n is 1 o 2, and X represents a fluorine atom, a chlorine atom o a bromine atom, and the substituent represented by X is at the 2-position and/or the 4-position of the benzene ring; or n is 0; and R¹, R² and R³ are independently selected from the group consisting of methyl gruops and ethyl groups.

15. The composition of claim 13, wherein the anti-fungal agent is selected from the group consisting of:
2-(4-chlorophenyl)-1-(1H-1,2,4-triazol-1-yl)-3-trimethylsilyl-2-propanol;
2-(4-fluorophenyl)-1-(1H-1,2,4-triazol-1-yl)-3-trimethylsilyl-2-propanol; and
3-(2,4-difluorophenyl)-1-(1H-1,2,4-triazol-1-yl)-3-trimethylsilyl-2-propanol.

16. A method for the prevention or treatment of fungal infections, which comprises applying or administering a fungicidally or fungistatically effective amount of an anti-fungal agent to an animal, wherein the anti-fungal agent is selected from the group consisting of compounds of formula (I) and pharmaceutically acceptable salts thereof, as claimed in claim 1.

17. The method of claim 16, wherein:

n is 1 or 2, and X represents a fluorine atom, a chlorine atom or a bromine atom, and the substituent represented by X is at the 2-position and/or the 4-position of the benzene ring; or n is 0; and R¹, R² and R³ are independently selected from the group consisting of methyl gruops and ethyl groups.

18. The method of claim 16, wherein the anti-fungal agent is selected from the group consisting of:
2-(4-chlorophenyl)-1-(1H-1,2,4-triazol-1-yl)-3-trimethylsilyl-2-propanol;
2-(4-fluorophenyl)-1-(1H-1,2,4-triazol-1-yl)-3-trimethylsilyl-2-propanol; and
2-(2,4-difluorophenyl)-1-(1H-1,2,4-triazol-1-yl)-3-trimethylsilyl-2-propanol.

19. An agricultural composition for the protection of plants and plant reproductive matter from fungal attack, which composition comprises a fungicidally or fungistatically effective amount of a compound of formula (I) or a salt thereof, as claimed in claim 1, in admixture with an agricultural carrier or diluent.

20. The composition of clam 19, wherein:

n is 1 or 2, and X represents a fluorine atom, a chlorine atom or a bromine atom, and the substituent represented by X is at the 2-position and/or the 4-position of the benzene ring; or n is 0; and R¹, R² and R³ are independently selected from the group consisting of methyl gruops and ethyl groups.

21. The composition of claim 19, wherein the anti-fungal agent is selected from the group consisting of:
2-(4-chlorophenyl)-1-(1H-1,2,4-triazol-1-yl)-3-trimethylsilyl-2-propanol;
2-(4-fluorophenyl)-1-(1H-1,2,4-triazol-1-yl)-3-trimethylsilyl-2-propanol; and
2-(2,4-difluorophenyl)-1-(1H-1,2,4-triazol-1-yl)-3-trimethylsilyl-2-propanol.

22. A method of protecting plants and plant reproductive matter from fungal attack, which method comprises applying to said plants or plant reproductive matter or to a locus including the same a fungicidally or fungistatically effective amount of a compound of formula (I) or a salt thereof, as claimed in claim 1.

23. The method of claim 22, wherein:

A represents a 1,2,4-triazol-1-yl group;

n is 1 or 2, and X represents a fluorine atom, a chlorine atom or a bromine atom, and the substituent represented by X is at the 2-position and/or the 4-position of the benzene ring; or n is 0; and R¹, R² and R³ are independently selected from the group consisting of methyl gruops and ethyl groups.

24. The method of claim 22, wherein the anti-fungal agent is selected from the group consisting of:
2-(4-chlorophenyl)-1-(1H-1,2,4-triazol-1-yl)-3-trimethylsilyl-2-propanol;
2-(4-fluorophenyl)-1-(1H-1,2,4-triazol-1-yl)-3-trimethylsilyl-2-propanol; and
2-(2,4-difluorophenyl)-1-(1H-1,2,4-triazol-1-yl)-3-trimethylsilyl-2-propanol.

* * * * *

UNITED STATES PATENT AND TRADEMARK OFFICE
CERTIFICATE OF CORRECTION

PATENT NO. : 5,306,712
DATED : April 26, 1994
INVENTOR(S) : TOBITSUKA et al It is certified that error appears in the above-identified patent and that said Letters Patent is hereby corrected as shown below:

Column 49, line 11 (Claim 7): after "group," insert --and--.

Column 49, line 13 (Claim 7): delete "pl".

Column 49, line 23 (Claim 8): after "methyl" delete "gruops" and insert --groups--.

Column 49, line 51 (Claim 14): after "1" delete "o" and insert --or--.
line 52: after "atom" delete "o" and insert --or--.

Column 49, line 65 (Claim 15): at beginning of line, delete "3" and insert --2--.

Signed and Sealed this

Twenty-fourth Day of October, 1995

Attest:

BRUCE LEHMAN

*Attesting Officer*          *Commissioner of Patents and Trademarks*